(12) United States Patent
Dal Degan et al.

(10) Patent No.: US 9,789,181 B2
(45) Date of Patent: Oct. 17, 2017

(54) PAN-DR BINDING POLYPEPTIDES AND USES THEREOF

(71) Applicant: Epimmune Inc., San Diego, CA (US)

(72) Inventors: Florence Dal Degan, Cheney (FR); Mark J. Newman, Duluth, GA (US); Jeffery L. Alexander, San Diego, CA (US); Scott Southwood, Santee, CA (US)

(73) Assignee: EPIMMUNE INC., San Diego, CA (US)

( * ) Notice: Subject to any disclaimer, the term of this patent is extended or adjusted under 35 U.S.C. 154(b) by 0 days.

(21) Appl. No.: 14/978,829

(22) Filed: Dec. 22, 2015

(65) Prior Publication Data

US 2016/0114035 A1    Apr. 28, 2016

Related U.S. Application Data

(62) Division of application No. 13/146,607, filed as application No. PCT/EP2010/050839 on Jan. 26, 2010, now Pat. No. 9,249,187.

(60) Provisional application No. 61/147,892, filed on Jan. 28, 2009.

(30) Foreign Application Priority Data

Jan. 28, 2009   (EP) .................................... 09151495

(51) Int. Cl.
| | |
|---|---|
| C07K 7/08 | (2006.01) |
| C07K 19/00 | (2006.01) |
| A61K 39/00 | (2006.01) |
| A61K 39/39 | (2006.01) |
| C07K 14/74 | (2006.01) |

(52) U.S. Cl.
CPC ................ *A61K 39/39* (2013.01); *C07K 7/08* (2013.01); *A61K 2039/55516* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,736,142 | A | 4/1998 | Sette et al. |
| 6,413,935 | B1 | 7/2002 | Sette et al. |
| 6,602,510 | B1 | 8/2003 | Fikes et al. |
| 9,249,187 | B2 | 2/2016 | Degan et al. |
| 2008/0032921 | A1 | 2/2008 | Alexander et al. |

FOREIGN PATENT DOCUMENTS

| | | |
|---|---|---|
| WO | WO 95/07707 | 3/1995 |
| WO | WO 2004/052917 A2 | 6/2004 |
| WO | WO 2004/094454 A2 | 11/2004 |
| WO | WO 2005/012502 A2 | 2/2005 |
| WO | WO 2005/120563 A2 | 12/2005 |
| WO | WO 2007/137586 A2 | 12/2007 |

OTHER PUBLICATIONS

Fraser et al (Vaccine, 2014, 32: 2896-2903).*
Alexander, J., et al., "The Optimization of Helper T Lymphocyte (HTL) Function in Vaccine Development," *Immunol. Res.* 18:79-92, Humana Press, Inc., United States (1998).
International Search Report for International Application No. PCT/EP2010/050839, mailed on Oct. 6, 2010, European Patent Office, Netherlands, 10 pages.
Written Opinion of the International Searching Authority for International Application No. PCT/EP2010/050839, mailed on Oct. 6, 2010, European Patent Office, Netherlands, 14 pages.
Alexander, J., et al., "Development of High Potency Universal DR-Restricted Helper Epitopes by Modification of High Affinity DR-Blocking Peptides," *Immunity* 1:751-761, Cell Press, United States (1994).
Busch, R., et al., "Degenerate binding of immunogenic peptides to HLA-DR proteins on B cell surfaces," *Int. Immunol.* 2:443-451, Oxford University Press, England (1990).
Hill, C.M., et al., "Conformational and Structural Characteristics of Peptides Binding to HLA-DR Molecules," *J. Immunol.* 147:189-197, The American Association of Immunologists, United States (1991).
O'Sullivan, D., et al., "On the Interaction of Promiscuous Antigenic Peptides With Different DR Alleles," *J. Immunol.* 147:2663-2669, The American Association of Immunologists, United States (1991).
Panina-Bordignon, P., et al., "Universally immunogenic T cell epitopes: promiscuous binding to human MHC class II and promiscuous recognition by T cells," *Eur. J. Immunol.* 19:2237-2242, Wiley-VCH, Germany (1989).
Roche, P.A. and Cresswell, P., "High-Affinity Binding of an Influenza Hemagglutinin-Derived Peptide to Purified HLA-DR," *J. Immunol.* 144:1849-1856, The American Association of Immunologists, United States (1990).
Sinigaglia, F., et al., "A malaria T-cell epitope recognized in association with most mouse and human MHC class II molecules," *Nature* 336:778-780, Nature Publishing Group, England (1988).

* cited by examiner

*Primary Examiner* — Gerald R Ewoldt
*Assistant Examiner* — Marianne Dibrino
(74) *Attorney, Agent, or Firm* — Sterne, Kessler, Goldstein and Fox P.L.L.C.

(57) ABSTRACT

The present invention provides novel artificial oligopeptides capable of binding HLA Class II molecules encoded by several alleles. The oligopeptides include the sequence $AX_1FVAAX_2TLX_3AX_4A$ (SEQ ID NO:1), wherein $X_1$ is H; $X_2$ is selected from the group consisting of F, N, Y and W; $X_3$ is H and $X_4$ is selected from the group consisting of A, D and E. The invention also relates to large peptides comprising the oligopeptides, polynucleotides encoding the oligopeptides and larger peptides, as well as to compositions comprising the oligopeptides, peptides or polynucleotides. Also disclosed are methods for inducing immune responses.

12 Claims, 3 Drawing Sheets

| SEQ ID NO: | PADRE analog | IC₅₀ nM to purified HLA | | | | | | | | | | | | | No. alleles IC₅₀ ≤1000nM |
|---|---|---|---|---|---|---|---|---|---|---|---|---|---|---|---|
| | | DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | |
| 3 | | 4.0 | 289 | 1.4 | 0.79 | 32 | 97 | 9.5 | 50 | 9.1 | 367 | 37 | 447 | 19 | 13 |
| 4 | | 3.3 | 209 | 2.6 | 2.9 | 25 | 49 | 5.2 | 28 | 11 | 648 | 9.8 | 207 | 5.4 | 13 |
| 5 | W4 | 2.6 | 161 | 3.1 | 3.8 | 18 | 82 | 8.5 | 35 | 14 | 2931 | 31 | 566 | 9.3 | 12 |
| 6 | H12 | 3.9 | 146 | 3.4 | 2.4 | 17 | 35 | 7.6 | 24 | 14 | 656 | 15 | 209 | 22 | 13 |
| 7 | W4.H12 | 4.3 | 111 | 2.6 | 2.0 | 15 | 84 | 8.1 | 33 | 32 | 4240 | 36 | 447 | 28 | 12 |
| 8 | W4.Y9.H12 | 3.9 | 160 | 3.8 | 3.2 | 24 | 91 | 6.8 | 19 | 14 | 3110 | 6.2 | 460 | 25 | 12 |
| 9 | W4.F9.H12 | 5.3 | 139 | 3.1 | 2.5 | 21 | 69 | 10 | 18 | 18 | 21,831 | 38 | 115 | 30 | 12 |
| 10 | W4.N9.H12 | 3.8 | 174 | 2.9 | 5.5 | 21 | 43 | 8.6 | 33 | 16 | 38 | 101 | 606 | 22 | 13 |
| 11 | F4 | 5.7 | 227 | 2.4 | 7.3 | 31 | 74 | 12 | 31 | 27 | 2811 | 32 | 517 | 9.9 | 12 |
| 12 | F4.H12 | 3.6 | 129 | 2.2 | 2.9 | 21 | 60 | 7.8 | 18 | 14 | 4103 | 25 | 440 | 13 | 12 |
| 13 | F4.Y9.H12 | 4.4 | 151 | 1.7 | 2.3 | 19 | 54 | 7.4 | 15 | 13 | 5287 | 4.8 | 805 | 11 | 12 |
| 14 | F4.F9.H12 | 5.5 | 371 | 2.0 | 1.1 | 17 | 610 | 82 | 48 | 18 | 218,750 | 25 | 129 | 29 | 12 |
| 15 | F4.N9.H12 | 6.5 | 285 | 3.8 | 4.1 | 27 | 82 | 28 | 31 | 42 | 187 | 70 | 876 | 26 | 13 |
| 16 | F4.D14 | 7.2 | 2938 | 5.3 | 2.7 | 22 | 91 | 20 | 32 | 65 | 7053 | 64 | 13,928 | 13 | 10 |
| 17 | F4.Y9.D14 | 3.8 | 2026 | 5.0 | 6.0 | 33 | 45 | 6.7 | 12 | 55 | 856 | 25 | 19,927 | 7.3 | 11 |
| 18 | F4.F9.D14 | 43 | 49,855 | 4.5 | 6.1 | 8.4 | 5378 | 108 | 113 | 57 | 58,333 | 66 | 12,459 | 9.4 | 9 |
| 19 | F4.N9.D14 | 3.4 | 140 | 4.0 | 4.5 | 9.5 | 74 | 16 | 18 | 46 | 187 | 103 | 5522 | 4.4 | 12 |
| 20 | Y4 | 2.7 | 108 | 1.6 | 1.4 | 6.6 | 74 | 6.1 | 12 | 11 | 917 | 13 | 291 | 5.9 | 13 |
| 21 | Y4.H12 | 3.7 | 119 | 2.6 | 2.6 | 6.9 | 55 | 9.7 | 18 | 18 | 1561 | 16 | 279 | 15 | 12 |
| 22 | Y4.Y9.H12 | 2.5 | 77 | 2.3 | 1.9 | 7.3 | 65 | 5.2 | 11 | 12 | 830 | 4.0 | 445 | 12 | 13 |
| 23 | Y4.F9.H12 | 3.4 | 126 | 1.0 | 0.67 | 4.4 | 78 | 5.9 | 13 | 17 | 2955 | 16 | 81 | 18 | 12 |
| 24 | Y4.N9.H12 | 4.5 | 130 | 3.3 | 5.2 | 13 | 49 | 12 | 21 | 14 | 54 | 53 | 703 | 16 | 13 |
| 25 | H4 | 4.7 | 262 | 3.1 | 4.8 | 23 | 110 | 12 | 45 | 13 | 1527 | 20 | 384 | 11 | 12 |
| 26 | H4.H12 | 4.2 | 198 | 2.5 | 2.5 | 12 | 53 | 9.3 | 21 | 14 | 1194 | 12 | 267 | 23 | 12 |
| 27 | H4.Y9.H12 | 3.8 | 214 | 3.4 | 5.7 | 23 | 94 | 11 | 26 | 16 | 1321 | 4.2 | 526 | 30 | 12 |

FIG. 1

| SEQ ID NO: | PADRE analog | IC$_{50}$nM to purified HLA | | | | | | | | | | | | | No. alleles IC$_{50}$ <1000nM |
|---|---|---|---|---|---|---|---|---|---|---|---|---|---|---|---|
| | | DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | |
| 28 | H4.F9.H12 | 4.0 | 228 | 2.2 | 3.1 | 8.6 | 49 | 11 | 24 | 8.1 | 1549 | 13 | 100 | 15 | 12 |
| 29 | H4.N9.H12 | 4.1 | 361 | 4.5 | 6.8 | 18 | 76 | 17 | 37 | 22 | 47 | 73 | 862 | 33 | 13 |
| 30 | D14 | 5.0 | 1159 | 7.3 | 9.7 | 17 | 56 | 26 | 27 | 59 | 807 | 19 | 2369 | 19 | 11 |
| 31 | H4.D14 | 5.1 | 1694 | 8.5 | 7.1 | 15 | 43 | 24 | 39 | 63 | 675 | 29 | 2100 | 23 | 11 |
| 32 | H4.Y9.D14 | 5.4 | 1693 | 11 | 9.6 | 25 | 48 | 34 | 31 | 43 | 502 | 11 | 3798 | 17 | 11 |
| 33 | H4.F9.D14 | 6.7 | 2138 | 15 | 9.5 | 19 | 83 | 26 | 30 | 76 | 594 | 37 | 948 | 42 | 12 |
| 34 | H4.N9.D14 | 6.1 | 3116 | 21 | 13 | 36 | 88 | 67 | 60 | 31 | 199 | 172 | 6394 | 18 | 11 |
| 35 | E14 | 5.5 | 530 | 6.5 | 4.7 | 8.4 | 59 | 21 | 41 | 36 | 699 | 23 | 710 | 17 | 13 |
| 36 | H4.E14 | 5.1 | 1118 | 6.4 | 4.7 | 7.5 | 54 | 22 | 44 | 53 | 1103 | 20 | 677 | 18 | 11 |
| 37 | H4.Y9.E14 | 6.9 | 885 | 7.5 | 5.3 | 11 | 59 | 25 | 35 | 44 | 1007 | 10 | 721 | 16 | 12 |
| 38 | H4.F9.E14 | 6.8 | 855 | 6.4 | 8.1 | 8.1 | 49 | 19 | 46 | 41 | 801 | 31 | 526 | 19 | 13 |
| 39 | H4.N9.E14 | 7.1 | 1843 | 12 | 14 | 36 | 83 | 64 | 59 | 68 | 234 | 255 | 941 | 20 | 12 |
| 40 | D4 | 7.0 | 330 | 5.1 | 4.0 | 30 | 195 | 17 | 57 | 19 | 4002 | 64 | 1537 | 20 | 11 |
| 41 | D4.H12 | 4.9 | 249 | 5.3 | 7.1 | 27 | 152 | 24 | 40 | 28 | 4445 | 89 | 1533 | 59 | 11 |
| 42 | D4.Y9.H12 | 4.8 | 286 | 4.5 | 5.3 | 21 | 182 | 14 | 32 | 40 | 4875 | 19 | 2486 | 51 | 11 |
| 43 | D4.F9.H12 | 7.3 | 746 | 4.7 | 3.7 | 11 | 223 | 43 | 59 | 44 | 15.190 | 97 | 1047 | 57 | 11 |
| 44 | D4.N9.H12 | 7.8 | 731 | 6.6 | 8.6 | 43 | 196 | 44 | 82 | 57 | 187 | 580 | 4917 | 80 | 12 |
| 45 | E4 | 2.5 | 169 | 3.8 | 2.8 | 9.8 | 81 | 16 | 41 | 45 | 840 | 56 | 332 | 6.7 | 13 |
| 46 | E4.H12 | 5.1 | 134 | 3.1 | 4.1 | 27 | 97 | 24 | 44 | 38 | 1152 | 51 | 350 | 48 | 12 |
| 47 | E4.Y9.H12 | 3.9 | 144 | 2.3 | 3.2 | 17 | 161 | 13 | 28 | 27 | 1453 | 6.9 | 448 | 52 | 12 |
| 48 | E4.F9.H12 | 6.1 | 276 | 2.1 | 2.6 | 14 | 140 | 19 | 18 | 48 | 2015 | 50 | 132 | 39 | 12 |
| 49 | E4.N9.H12 | 9.0 | 276 | 3.5 | 6.9 | 44 | 158 | 37 | 87 | 70 | 183 | 137 | 878 | 55 | 13 |
| 50 | N4 | 4.4 | 372 | 1.8 | 5.9 | 18 | 66 | 8.5 | 62 | 14 | 1609 | 12 | 469 | 6.7 | 12 |
| 51 | N4.H12 | 4.5 | 147 | 1.8 | 1.5 | 7.6 | 53 | 13 | 43 | 11 | 1157 | 10 | 253 | 20 | 12 |
| 52 | N4.Y9.H12 | 2.7 | 171 | 1.8 | 5.2 | 19 | 67 | 7.5 | 25 | 16 | 1431 | 4.2 | 567 | 20 | 12 |

FIG. 1 (cont'd)

| SEQ ID NO: | PADRE analog | DRB1 *0101 | DRB1 *0301 | DRB1 *0401 | DRB1 *0404 | DRB1 *0405 | DRB1 *0701 | DRB1 *0802 | DRB1 *0901 | DRB1 *1101 | DRB1 *1302 | DRB1 *1501 | DRB4 *0101 | DRB5 *0101 | No. alleles IC$_{50}$ <1000nM |
|---|---|---|---|---|---|---|---|---|---|---|---|---|---|---|---|
| 53 | M4.F9.H12 | 4,7 | 254 | 1,6 | 3,9 | 12 | 52 | 12 | 41 | 16 | 2017 | 16 | 111 | 27 | 12 |
| 54 | M4.N9.H12 | 6,1 | 396 | 3,4 | 8,3 | 48 | 84 | 32 | 72 | 25 | 44 | 114 | 1106 | 43 | 12 |
| 55 | M4.D14 | 7,6 | 1664 | 5,5 | 9,7 | 16 | 52 | 35 | 84 | 41 | 865 | 20 | 2513 | 24 | 11 |
| 56 | M4.Y9.D14 | 8,5 | 1529 | 6,3 | 15 | 30 | 71 | 22 | 44 | 100 | 819 | 12 | 4731 | 30 | 11 |
| 57 | M4.F9.D14 | 10 | 2331 | 4,3 | 12 | 13 | 56 | 37 | 55 | 74 | 1022 | 24 | 2883 | 20 | 10 |
| 58 | M4.N9.D14 | 8,5 | 2732 | 9,7 | 23 | 46 | 98 | 64 | 109 | 128 | 269 | 296 | 6324 | 29 | 11 |
| 59 | M4.E14 | 1,8 | 723 | 2,8 | 5,8 | 3,8 | 55 | 19 | 58 | 56 | 1044 | 31 | 221 | 15 | 12 |
| 60 | M4.Y9.E14 | 6,9 | 1070 | 13 | 6,1 | 48 | 68 | 21 | 43 | 60 | 590 | 11 | 718 | 25 | 12 |
| 61 | M4.F9.E14 | 8,0 | 1543 | 5,8 | 5,0 | 12 | 57 | 14 | 55 | 18 | 1570 | 29 | 492 | 16 | 11 |
| 62 | M4.N9.E14 | 9,3 | 1743 | 30 | 11 | 45 | 107 | 48 | 64 | 78 | 195 | 259 | 964 | 34 | 12 |
| 63 | Q4 | 5,1 | 271 | 1,6 | 2,1 | 21 | 58 | 8,3 | 39 | 12 | 697 | 17 | 259 | 5,2 | 13 |
| 64 | Q4.H12 | 5,0 | 187 | 1,5 | 1,5 | 13 | 53 | 8,3 | 32 | 18 | 1122 | 13 | 265 | 23 | 12 |
| 65 | Q4.Y9.H12 | 4,2 | 153 | 2,2 | 1,9 | 22 | 57 | 5,1 | 21 | 17 | 700 | 3,6 | 428 | 24 | 13 |
| 66 | Q4.F9.H12 | 5,3 | 325 | 2,7 | 4,4 | 7,7 | 58 | 13 | 31 | 27 | 953 | 18 | 97 | 23 | 13 |
| 67 | Q4.N9.H12 | 5,9 | 319 | 3,3 | 6,9 | 38 | 76 | 24 | 56 | 44 | 33 | 78 | 525 | 45 | 13 |
| 68 | I4 | 4,0 | 393 | 2,1 | 1,6 | 38 | 75 | 14 | 61 | 25 | 370 | 7,3 | 124 | 5,6 | 13 |
| 69 | I4.H12 | 6,0 | 205 | 2,6 | 3,7 | 13 | 78 | 12 | 38 | 28 | 891 | 9,4 | 84 | 32 | 13 |
| 70 | I4.Y9.H12 | 5,7 | 301 | 2,8 | 2,6 | 20 | 95 | 9,4 | 48 | 19 | 1950 | 3,2 | 346 | 26 | 12 |
| 71 | I4.F9.H12 | 12 | 442 | 1,9 | 2,7 | 14 | 206 | 36 | 80 | 12 | 6790 | 9,7 | 117 | 21 | 12 |
| 72 | I4.N9.H12 | 7,3 | 245 | 2,7 | 4,5 | 18 | 109 | 27 | 75 | 36 | 65 | 17 | 109 | 37 | 13 |

PAN-DR BINDING POLYPEPTIDES AND USES THEREOF

CROSS REFERENCE TO RELATED APPLICATIONS

This application is a divisional application of U.S. application Ser. No. 13/146,607, filed Jul. 27, 2011, now U.S. Pat. No. 9,249,187, which is a U.S. National Stage of International Application No. PCT/EP2010/050839, filed Jan. 26, 2010, said International Application No. PCT/EP2010/050839 claims the benefits of U.S. provisional application No. 61/147,892, and EP application number 09151495.0, both filed on Jan. 28, 2009, all of which are herein incorporated by reference.

REFERENCE TO A SEQUENCE LISTING SUBMITTED ELECTRONICALLY VIA EFS-WEB

The content of the electronically submitted sequence listing (Name: 2473_0660002_SeqListingUPDATED_02152017_ST25.txt, Size: 45,883 bytes; and Date of Creation: Feb. 15, 2017) filed herewith was originally filed with the U.S. application Ser. No. 13/146,607 and is incorporated herein by reference in its entirety.

BACKGROUND OF THE INVENTION

Immunogenic peptides, containing epitopes recognized by T helper cells, have been found to be useful in inducing immune responses. The use of helper peptides to enhance antibody responses against particular determinants is described for instance in Hervas-Stubbs, et al., *Vaccine* 12:867-871 (1994).

Although allele-specific polymorphic residues that line the peptide binding pockets of MHC alleles tend to endow each allele with the capacity to bind a unique set of peptides, there are instances in which a given peptide has been shown to bind to more than one MHC allele. For example, several investigators reported degenerate binding and/or recognition of certain epitopes in the context of multiple DR types, leading to the concept that certain peptides might represent "universal" epitopes (Busch, et al., *Int. Immunol.* 2:443-451 (1990); Panina-Bordignon, et al., *Eur. J. Immunol.* 19:2237-2242 (1989); Sinigaglia, et al., *Nature* 336:778-780 (1988); O'Sullivan, et al., *J. Immunol.* 147:2663-2669 (1991); Roache, et al., *J. Immunol.* 144:1849-1856 (1991); Hill, et al., *J. Immunol.* 147:189-197 (1991)). Pan-DR binding peptides have been described in, for example, U.S. Pat. No. 6,413,935; WO 95/07707; WO/2005/120563; and Alexander, et al., *Immunity* 1:751-761 (1994). These peptides have been shown to help in the generation of various immune responses against antigens.

BRIEF SUMMARY OF THE INVENTION

The present invention is based on studies of the effects of selected mutations in the sequence of PADRE (SEQ ID NO: 3) in terms of providing immunogenic peptides (both in the form of short peptides, oligopeptides and polypeptides) having improved stability vs. proteolytic enzymes.

The invention thus relates to an isolated polypeptide comprising or consisting of an oligopeptide sequence that can bind an MEW class II molecule encoded by at least three different HLA-DR alleles with an $IC_{50}$ value of less than 100 nM, such as at least 50 nM, wherein the oligopeptide sequence comprises $AX_1FVAAX_2TLX_3AX_4A$ (SEQ ID NO:1), wherein $X_1$ is selected from the group consisting of W, F, Y, H, D, E, N, Q, I and K;

$X_2$ is selected from the group consisting of F, N, Y and W;

$X_3$ is selected from the group consisting of H and K, and $X_4$ is selected from the group consisting of A, D and E, with the proviso that the oligopeptide sequence is not AKFVAAWTLKAAA (SEQ ID NO: 3).

The invention further relates to polynucleotides encoding the polypeptides of the invention and to vectors including such polynucleotides. Also encompassed by the invention are cells comprising the polynucleotides of the invention. The invention further relates to compositions, including pharmaceutical compositions, comprising the polypeptides or oligopeptides or polynucleotides or vectors or cells of the invention. Finally, the invention relates to a method of stimulating an immune response by administering a polypeptide or oligopeptide or polynucleotide or vector or cell or composition of the invention to a subject in need thereof.

BRIEF DESCRIPTION OF THE DRAWING

FIG. 1 shows data from binding experiments determining the HLA-DR binding of peptides of the invention to various HLA-DR molecules, cf. Example 1 for details.

DEFINITIONS

Unless defined otherwise, all technical and scientific terms used herein generally have the same meaning as commonly understood by one of ordinary skill in the art to which this invention belongs. This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

The terms "oligopeptide" or "peptide" as used herein refer to a chain of at least four amino acid residues or amino acid mimetics. The oligopeptides or peptides can be a variety of lengths, either in their neutral (uncharged) forms or in salt forms, and either free of modifications, including but not limited to, glycosylation, side chain oxidation, or phosphorylation or containing one or more of these modifications. While optional modifications do not destroy the biological activity of the polypeptides described herein, however, the invention includes options in which the modifications reduce or eliminate biological activity (e.g., to limit activity until such modification if removed, e.g., in vivo).

The terms "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds. The terms further include polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof can be antigenic and immunogenic polypeptides.

The terms "amino acid residue," "amino acid" and "residue" when referring to an amino acid residue in a peptide, oligopeptide or protein are used interchangeably and, as used herein, mean an amino acid or amino acid mimetic joined covalently to at least one other amino acid or amino acid mimetic through an amide bond or amide bond mimetic.

As used herein, the term "amino acid," when unqualified, refers to an "L-amino acid" or L-amino acid mimetic.

As used herein, the nomenclature used to describe peptide compounds follows the conventional practice wherein the amino group is presented to the left (the N-terminus) and the carboxyl group to the right (the C-terminus) of each amino acid residue. When amino acid residue positions are referred to in an epitope, they are numbered in an amino to carboxyl direction with position one being the position closest to the amino terminal end of the epitope, or the peptide or protein of which it may be a part. In the amino acid structure formulae, each residue is generally represented by standard three-letter or single-letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

As used herein, the symbols for the amino acids are shown below.

| Single Letter Symbol | Three Letter Symbol | Amino Acids |
| --- | --- | --- |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The term "pan DR-binding peptide" or "pan-DR binding epitope" as used herein refers to a member of a family of molecules that binds more than one MHC class II DR molecule (e.g., binding each of the more than one MHC molecule with an $IC_{50}$ of less than 100 nM, such as at least 50 nM). In some embodiments, the pan DR-binding oligopeptides of the present invention are peptides capable of binding at least 2, 3, 4, 5, 6, 7, 8, 9, 10, 11, or all 12 most common DR alleles (DR1, 2w2b, 2w2a, 3, 4w4, 4w14, 5, 7, 52a, 52b, 52c, and 53). The pan-DR binding oligopeptides of the present invention, in addition to promoting an immune response against a second determinant, can also serve as target immunogens themselves. Thus, for instance, in the case in which the pan-DR binding peptide itself is linked to a carbohydrate epitope, the immune response may be to both the pan-DR binding peptide and the carbohydrate epitope.

As used herein, the term "PADRE" refers to the pan DR binding peptide having the amino acid sequence AKFVAAWTLKAAA (SEQ ID NO: 3).

As used herein, the expression "PADRE analogue" refers to a pan DR peptide comprising an amino acid sequence which, compared to PADRE, includes at most 1, 2, 3 or 4 amino acid changes, of which at least one is made in K2, W7, K10 or A12.

As used herein, the term "$IC_{50}$" refers to the concentration of peptide in a binding assay at which 50% inhibition of binding of a reference peptide is observed. Depending on the conditions in which the assays are run (i.e., limiting MHC proteins and labeled peptide concentrations), these values may approximate $K_D$ values. Assays for determining binding are described in detail, e.g., in PCT publications WO 94/20127 and WO 94/03205, the disclosure of each which is herein incorporated by reference. It should be noted that $IC_{50}$ values can change, often dramatically, if the assay conditions are varied, and depending on the particular reagents used (e.g., MHC preparation, etc.). For example, excessive concentrations of MHC molecules will increase the apparent measured $IC_{50}$ of a given ligand.

Alternatively, binding is expressed relative to a reference peptide, for instance PADRE. Although as a particular assay becomes more, or less, sensitive, the $IC_{50}$ value of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide. Binding may also be determined using other assay systems including those using: live cells (e.g., Ceppellini et al., Nature 339:392, 1989; Christnick et al., Nature 352:67, 1991; Busch et al., Int. Immunol. 2:443, 19990; Hill et al., J. Immunol. 147:189, 1991; del Guercio et al., J. Immunol. 154:685, 1995), cell free systems using detergent lysates (e.g., Cerundolo et al., J. Immunol. 21:2069, 1991), immobilized purified MHC (e.g., Hill et al., J. Immunol. 152, 2890, 1994; Marshall et al., J. Immunol. 152:4946, 1994), ELISA systems (e.g., Reay et al., EMBO J. 11:2829, 1992), surface plasmon resonance (e.g., Khilko et al., J. Biol. Chem. 268:15425, 1993); high flux soluble phase assays (Hammer et al., J. Exp. Med. 180:2353, 1994), and measurement of class I MHC stabilization or assembly (e.g., Ljunggren et al., Nature 346:476, 1990; Schumacher et al., Cell 62:563, 1990; Townsend et al., Cell 62:285, 1990; Parker et al., J. Immunol. 149:1896, 1992).

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The term "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form. A "multi-epitope construct" can be used interchangeably with the term "minigene" or "multi-epitope nucleic acid vaccine," and comprises multiple epitope nucleic acids that encode peptide epitopes of any length that can bind to a molecule functioning in the immune system, e.g., in some embodiments, a MHC class I and a T-cell receptor and/or a MHC class II and a T-cell receptor. Epitope nucleic acids in a multi-epitope construct can encode, for example, class II MHC epitopes or a combination of class I MHC epitopes and class II MHC epitopes.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor or MHC molecule. Thus, the term "epitope" includes, but is not limited to, immunogenic peptides of the invention capable of binding to an appropriate MHC molecule and thereafter inducing a cytotoxic T cell response, or a helper T cell response, or alternatively, capable of binding an antibody, and thereafter inducing an antibody response to the antigen from which the immunogenic peptide is derived.

A "flanking residue" is a residue that is positioned next to an epitope. A flanking residue can be introduced or inserted at a position adjacent to the N-terminus or the C-terminus of an epitope.

The terms "immunogen" and "antigen" are used interchangeably and mean any compound to which a cellular or humoral immune response is to be directed against. Furthermore, antigenic or immunogenic peptides of the invention may be linear, i.e., be comprised of contiguous amino acids in a polypeptide, or, in the case of antibody-epitopes, may be three dimensional or conformational, i.e., where a functional epitope is comprised of non-contiguous amino acids which come together due to the secondary or tertiary structure of the polypeptide, thereby forming an epitope.

As used herein, the term "antigenic determinant" is any structure that can elicit, facilitate, or be induced to produce an immune response, for example carbohydrate epitopes, lipids, proteins, peptides, or combinations thereof.

The term "antibody" refers to a polypeptide substantially encoded by an immunoglobulin gene or genes, that is capable of interacting with and binding to a specified protein or antigen contained in a composition comprising, but not limited to, one or more proteins and/or antigens.

The term "CTL epitope" refers to a peptide, which is recognized and bound by a particular MHC class I molecule, and which is recognized by a T lymphocyte when complexed with the particular MHC Class I molecule. In some embodiments, the CTL epitope can be from about 8 to about 13 amino acids in length, from about 9 to about 11 amino acids in length, or from about 9 to about 10 amino acids in length.

The term "HTL epitope" refers to a peptide, which is recognized and bound by a particular MHC class II molecule, and which is recognized by a T lymphocyte when complexed with the particular MHC Class II molecule. In some embodiments, the HTL epitope can be from about 6 to about 30 amino acids in length, from about 8 to about 30 amino acids in length, from about 10 to about 30 amino acids, from about 12 to about 30 amino acids in length, from about 6 to about 25 amino acids in length, from about 8 to about 25 amino acids in length, from about 10 to about 25 amino acids, from about 12 to about 25 amino acids in length, from about 6 to about 18 amino acids in length, from about 8 to about 18 amino acids in length, from about 10 to about 18 amino acids, or from about 12 to about 18 amino acids in length.

When stating that a T lymphocyte "recognizes" a complex between an MHC molecule and a CTL or HTL epitope is herein mean that the T-cell receptors on the T lymphocyte bind to the complex with the effect that the T lymphocyte is activated.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The phrases "isolated" or "biologically pure" refer to material which is substantially or essentially free from components which normally accompany it as found in its native state.

The term "linker" as used herein is any compound used to provide covalent linkage and spacing between two functional groups (e.g., a pan-DR binding peptide and a desired immunogen). In some embodiments, the linker comprises neutral molecules, such as aliphatic carbon chains, amino acids or amino acid mimetics, which are substantially uncharged under physiological conditions and may have linear or branched side chains. In some cases, the linker can, itself, be immunogenic. Various linkers useful in the invention are described in more detail, below. Additionally, the verbs "link" and "conjugate" are used interchangeably herein and refer to covalent attachment of two or more species.

The terms "link" or "join" refers to any method known in the art for functionally connecting peptides, including, without limitation, recombinant fusion, covalent bonding, disulfide bonding, ionic bonding, hydrogen bonding, and electrostatic bonding.

The term "directly linked" or "directly joined" refers to being joined without anything intervening. For example, in the case of two peptides being directly joined, one peptide would be joined or bonded to another peptide, as described above, without any sequence, molecule, spacer, linker, etc. intervening between the two peptides. Directly joined peptides may or may not share amino acids in common, i.e., the sequences of the two peptides are allowed to not overlap and also to overlap; the latter is e.g. relevant if a PADRE analogue of the invention is introduced in another (poly) peptide by means of insertion—in order to ensure the presence of the PADRE analogue's amino acid sequence, it is in only necessary to insert those amino acid residues which together with the amino acid residues at the insertion point provides for the entire sequence for the PADRE analogue.

The term "indirectly linked" refers to being joined with something intervening. For example, in the case of two peptides being indirectly joined, one peptide would be joined or bonded to another peptide, as described above, with a sequence, molecule, spacer, linker, etc. intervening between the two peptides.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, e.g., Paul, Fundamental Immunology, 3rd ed., Raven Press, New York, 1993.

The phrase "pharmaceutically acceptable" refers to a generally non-toxic, inert, and/or physiologically compatible composition.

DETAILED DESCRIPTION

I. Introduction

The inventors have discovered a new class of peptides that are pan-DR binders, i.e., the peptides bind to MHC class II molecules encoded by a number of different DR alleles, thereby allowing the peptides to stimulate an immune response in a wide spectrum of individuals. Further, the inventors have discovered that a number of the new peptides have significantly improved protease resistance, thereby allowing for a longer in vivo half-life. Surprisingly, some of these peptides reflect a greatly increased ability to boost an immune response over known pan-DR peptides.

A biological activity of the polypeptides of the invention (or fragments thereof) is the ability to bind an appropriate MHC molecule and induce a T helper response, which optionally helps to induce an immune response against a target immunogen or immunogen mimetic. In the case of peptides useful for stimulating antibody responses, the peptides of the invention will induce a T helper response, which in turn helps induce a humoral response against the target immunogen.

II. Pan-DR Binding Peptides

The present invention provides a new class of peptides that are pan-DR binding peptides and provides uses thereof. The peptides of the present invention are capable of binding more than one of a number of different DR alleles and thus find use in increasing immune responses to various antigens/immunogens. The peptides of the present invention further find use in eliciting an enhanced immune response over known pan-DR binding peptides, for example, as disclosed in U.S. Pat. No. 5,736,142.

As demonstrated herein, the inventors have identified a series of peptide sequences that bind to MHC molecules encoded by multiple HLA alleles. Partly in view of this data, the inventors have determined that the sequence motifs below represent pan-DR binding peptides with improved activity and immunogenicity. In some embodiments, the polypeptides of the present invention comprise an oligopeptide sequence that can bind an MHC molecule encoded by at least 2, 3, 4, 5, 6, 7, 8, 9, 10, 11, 12, or more different DR alleles, wherein the oligopeptide sequence comprises $AX_1FVAAX_2TLX_3AX_4A$ (SEQ ID NO:1), wherein $X_1$ is selected from the group consisting of W, F, Y, H, D, E, N, Q, I and K; $X_2$ is selected from the group consisting of F, N, Y and W; $X_3$ is selected from the group consisting of H and K, and $X_4$ is selected from the group consisting of A, D and E. In some embodiments, the polypeptide comprises an oligopeptide sequence that can bind an MHC molecule encoded by at least 2, 3, 4, 5, 6, 7, 8, 9, 10, 11, 12, or more different DR alleles, wherein the oligopeptide sequence comprises $AX_1FVAAX_2TLHAAA$ (SEQ ID NO:2), wherein $X_1$ is selected from the group consisting of Y, H, I, E, N, Q and K; and $X_2$ is selected from the group consisting of F, N, Y and W. According to the inventions, the oligopeptide sequence does not comprise AKFVAAWTLKAAA (SEQ ID NO:3).

In some embodiments, the polypeptides of the present invention comprise one or more copies of one or more amino acid sequences constituting the 13 amino acid C-terminal fragment of an oligopeptide selected from SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, or SEQ ID NO: 72.

The pan-DR binding peptides of the present invention are capable of binding multiple different MHC alleles and can also be referred to as "helper peptides." In some embodiments, the pan-DR binding peptides are capable of binding MHC molecules encoded by 2, 3, 4, 5, 6, 7, 8, 9, 10, 11, 12 or more different MHC class II alleles. In some embodiments the response induced is an enhanced immune response. In some embodiments immune response is directed towards the pan-DR binding oligopeptides of the invention. Alternatively, or in addition, the binding of the pan-DR binding oligopeptides to an MHC molecule further enhances an immune response to a second antigen, e.g., a polypeptide comprising one or more CTL peptides and/or a humoral (i.e., antibody) response to a protein or non-protein antigen.

The pan-DR polypeptide sequences described herein can be used alone, or as part of a larger fusion protein or conjugate. Thus, the polypeptides of the invention can include additional amino acids at either or both termini in addition to the pan-DR peptide sequences set forth herein. For example, it can be desirable to include other amino acid sequences as tags or markers or to promote in vivo or in vitro stability or otherwise to include additional benefits as is generally understood in the art. Moreover, the polypeptides of the invention can comprise one, two, three or more copies of one or more pan-DR oligopeptide sequence in the polypeptide and/or include multiple different pan-DR oligopeptide sequences in the polypeptides of the invention. Moreover, the polypeptides can include at least one additional HTL oligopeptide and/or CTL oligopeptide and/or antibody-inducing polypeptide, for example where it is desirable to enhance the immune response to such sequences or to polypeptides comprising such sequences. In such embodiments, the pan-DR sequences described herein function as alternatives to traditional carrier proteins such as Keyhole Limpet hemocyanin, tetanus toxoid, and diphtheria toxoid or as alternatives for prior art universal T-helper epitopes.

The polypeptides of the invention can be of any length. In some embodiments, the polypeptides comprising at least one pan-DR binding oligopeptide sequence of the invention, and optionally other amino acid sequences, are no longer than e.g., 1000, 900, 800, 700, 600, 500, 400, 300, 200, 100, 80, 60, 50, 40, 30, 20, or 15 amino acids, but in many cases the polypeptides comprising the pan-DR binding oligopeptide(s) are of approximately the same length as a native polypeptide, which has been modified by introduction of one or a few of the pan-DR binding oligopeptides of the invention (so that the polypeptide includes a majority of a native polypeptide sequence). Some polypeptides of the invention including pan-DR binding oligopeptides of the invention are, on the other hand, "multi-epitope constructs", i.e. polypeptides comprising a plurality of epitopes derived from one or more antigens, where the epitopes are organized in a non-naturally occurring order with a view to optimizing antigenicity or immunogenicity of the construct. Hence, the multi-epitope expression products discussed below under the disclosure of the polynucleotides of the invention are also embodiments of the peptides of the invention.

In such multi-epitope constructs, the plurality of epitopes is typically selected from a plurality of CTL epitopes, a plurality of B-cell epitopes, a plurality of T helper lymphocyte epitopes, a plurality of CTL and B-cell epitopes, a plurality of CTL and T helper lymphocyte epitopes, a plurality of B-cell and T helper lymphocyte epitopes, and a plurality of B-cell, CTL and T helper lymphocyte epitopes. These epitopes may be derived from on single antigenic protein, but may also be derived from at least 2 different polypeptide antigens, and in turn, these may be from the same or different species (of e.g. bacteria, virus, and parasites).

In some embodiments, the pan-DR binding oligopeptide sequences can differ from the original sequence by being modified by terminal-$NH_2$ acylation, e.g., by alkanoyl ($C_1$-$C_{20}$) or thioglycolyl acetylation, terminal-carboxy amidation, e.g., ammonia, methylamine, etc. In some embodiments, these modifications may provide sites for linking to a support or other molecule.

The biological activity of the peptides identified above may be assayed in a variety of systems. Typically, the ability to inhibit antigen-specific T cell activation is tested. In one exemplary protocol, an excess of peptide is incubated with an antigen-presenting cell of known MHC expression, (e.g., DR1) and a T cell clone of known antigen specificity (e.g., tetanus toxin 830-843) and MHC restriction (again, DR1), and the immunogenic peptide itself (i.e., tetanus toxin 830-843). The assay culture is incubated for a sufficient time for T cell proliferation, such as four days, and proliferation is then measured using standard procedures, such as pulsing with [$^3$H]-thymidine during the last 18 hours of incubation. The percent inhibition, compared to the controls which do not receive peptide, is then calculated.

The capacity of peptides to inhibit antigen presentation in an in vitro assay has been correlated to the capacity of the peptide to inhibit an immune response in vivo. In vivo activity may be determined in animal models, for example, by administering an immunogen known to be restricted to the particular MHC molecule recognized by the peptide, and the immunomodulatory peptide. T lymphocytes are subsequently removed from the animal and cultured with a dose range of immunogen. Inhibition of stimulation is measured by conventional means, e.g., pulsing with [$^3$H]-thymidine, and comparing to appropriate controls. Certain experimental details will of course be apparent to the skilled artisan. See also, Adorini, et al., *Nature* 334: 623-625 (1988), incorporated herein by reference.

A large number of cells with defined MHC molecules, particularly MHC Class II molecules, are known and readily available from, for instance, the American Type Culture Collection (see, e.g., "Catalogue of Cell Lines and Hybridomas," 6th edition (1988) 10801 University Boulevard, Manassas, Va. 20110-2209, U.S.A.

Some embodiments of the oligopeptides of the present invention comprise modifications to the N- and C-terminal residues. As will be well understood by the artisan, the N- and C-termini may be modified to alter physical or chemical properties of the peptide, such as, for example, to affect binding, stability, bioavailability, ease of linking, and the like.

Optionally, modifications of peptides with various amino acid mimetics or D-amino acids, for instance at the N- or C-termini, can be used, and are useful for instance, in increasing the stability of the peptides in vivo. Such peptides may be synthesized as "inverso" or "retroinverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid containing peptides with or without substitutions can be capped with a D-amino acid to inhibit exopeptidase destruction of the immunogenic peptide.

In vivo stability of polypeptides can be assayed in a number of ways. For instance, peptidases and various biological media, such as human plasma and serum, have been used to test stability. See, e.g., Verhoef, et al., *Eur. J. Drug Metab. Pharmacokin.* 11:291-302 (1986); Walter, et al., *Proc. Soc. Exp. Biol. Med.* 148:98-103 (1975); Witter, et al., *Neuroendocrinology* 30:377-381 (1980); Verhoef, et al., *J. Endocrinology* 110:557-562 (1986); Handa, et al., *Eur. J. Pharmacol.* 70:531-540 (1981); Bizzozero, et al., *Eur. J. Biochem.* 122:251-258 (1982); Chang, *Eur. J. Biochem.* 151:217-224 (1985), all of which are incorporated herein by reference.

The peptides or analogs of the invention can be modified by altering the order or composition of certain residues, it being readily appreciated that certain amino acid residues essential for biological activity, e.g., those at critical contact sites, may generally not be altered without an adverse effect on biological activity. The non-critical amino acids need not be limited to those naturally occurring in proteins, such as L-α-amino acids, or their D-isomers, but may include non-protein amino acids as well, such as β-γ-δ-amino acids, as well as many derivatives of L-α-amino acids. An oligopeptide of the present invention can comprise either L-amino acids or D-amino acids, but usually not D-amino acids within a core binding region.

The peptides of the invention can be prepared in a wide variety of ways. In some embodiments, recombinant DNA technology is employed wherein a nucleotide sequence which encodes an immunogenic polypeptide of the invention is inserted into an expression vector, transformed or transfected into an appropriate host cell and cultivated under conditions suitable for expression. These procedures are generally known in the art, as described generally in Sambrook, et al., *Molecular Cloning, A Laboratory Manual*, Cold Spring Harbor Press, Cold Spring Harbor, N.Y. (1989). Alternatively, depending on their size, the polypeptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. Ed., Pierce Chemical Co. (1984), supra.

III. Polynucleotides

The present invention provides for polynucleotides encoding the polypeptides of the invention as described herein. For example, polynucleotides encoding a polypeptide comprising an oligopeptide sequence that can bind an MHC molecule encoded by at least 2, 3, 4, 5, 6, 7, 8, 9, 10, 11, 12, or more different DR alleles, wherein the oligopeptide sequence comprises $AX_1FVAAX_2TLX_3AA_4A$ (SEQ ID NO:1), wherein $X_1$ is selected from the group consisting of W, F, Y, H, D, E, N, Q, I and K; $X_2$ is selected from the group consisting of F, N, Y and W; $X_3$ is selected from the group consisting of H and K, and $A_4$ is selected from A, D, and E. In some embodiments, the polypeptide comprises an oligopeptide sequence that can bind an MHC molecule encoded by at least 2, 3, 4, 5, 6, 7, 8, 9, 10, 11, 12, or more different DR alleles, wherein the oligopeptide sequence comprises $AX_1FVAAX_2TLHAAA$ (SEQ ID NO:2), wherein $X_1$ is selected from the group consisting of Y, H, I, E, N, Q and K; and $X_2$ is selected from the group consisting of F, N, Y and W. According to the invention, the oligopeptide sequence does not comprise AKFVAAWTLKAAA (SEQ ID NO: 3). In some embodiments, the polynucleotides of the present invention encode one or more amino acid sequences, each constituting the 13 amino acid C-terminal fragment of a oligopeptide selected from SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, or SEQ ID NO: 72; the polynucleotides may encode polypeptides which include the sequences or truncates in fusion with other amino acid sequences. So, polynucleotides of the invention are provided that encode polypeptides, as disclosed herein, comprising two or more CTL and/or HTL oligopeptide sequences, including at least one pan-DR oligopeptide sequence of the invention.

Polynucleotide constructs of the present invention can encode any of the above-described peptides or polypeptides. For example, multiple class I and/or class II MHC epitopes and/or B-cell epitopes, for example, more than one class II MHC epitopes (i.e., at least one pan-DR-binding oligopeptide sequence as described herein, e.g., SEQ ID NOs: 1, 2 and 4-72) or a combination of class I WIC epitopes and class II MHC epitopes and B-cell epitopes. Class I MHC-encoding epitope nucleic acids are also referred to as "CTL epitope nucleic acids," and class II MHC-encoding epitope nucleic acids are referred to as "HTL epitope nucleic acids". "B-cell epitopes" are epitopes, either linear or conformational, which bind antibodies or B-cell receptors. Some multi-epitope constructs can have a portion of their sequence encoding class I WIC epitopes and/or B-cell epitopes and another portion encoding class II MHC epitopes. In some embodiments, the CTL epitope nucleic acids encode an epitope peptide of about eight to about thirteen amino acids in length, e.g., about eight to about eleven amino acids in length, e.g., about nine amino acids in length. The HTL epitope nucleic acids encode at least one pan-DR oligopeptide as described herein, but where more than one HTL epitope is included, other HTL epitopes can be used as well. In some embodiments, the polynucleotide constructs include, for example, five or more, ten or more, fifteen or more, twenty or more, or twenty-five or more epitope nucleic acids. All of the CTL epitope nucleic acids in a multi-epitope polynucleotide construct can be from one organism (e.g., the nucleotide sequence of every epitope nucleic acid may be present in HIV strains), or the multi-epitope construct can include epitope nucleic acids present in two or more different organisms (e.g., some epitopes from HIV and some from HCV). As described hereafter, one or more epitope nucleic acids in the multi-epitope construct may be flanked by a spacer nucleic acid.

As will be understood, nucleic acid constructs encoding B-cell epitope containing polypeptides linked to or otherwise including the PADRE analogues of the invention are an embodiment of the invention. Such nucleic acid constructs typically encode a fusion construct where the PADRE analogues present in the expression product do not interfere negatively with the conformation of B-cell epitopes from the polypeptide. In cases where the B-cell epitopes are linear, the B-cell epitopes may simply be fused to the PADRE analogues, so the provision of the encoding nucleic acid is relatively uncomplicated. When the B-cell epitopes are conformational, however, typical examples of introduction points for the PADRE analogue encoding nucleic acids are in flexible loops of the polypeptide or in flexible termini (where 3D-structure of the conformational epitopes is sought preserved, e.g. by using entire protein domains or even entire polypeptides), but it is also possible to introduce the PADRE analogue encoding nucleic acid in regions encoding e.g. intracellularly confined parts of the polypeptide in question, since these regions are not relevant for immune responses in vivo. The expression products of such nucleic acid constructs are useful as antibody inducing immunogens, because the PADRE analogue sequences introduced will provide for increased T-lymphocyte help in the elicitation of an immune response against the expression product. As such, the expression products may be used directly as immunogens (for antibody induction in e.g. a vaccine or an immunogenic composition used for antibody production in animals) or it may exert its effect after being expressed in vivo in an animal which has been subjected to nucleic acid immunization with the encoding nucleic acid.

A "spacer" refers to a sequence that is inserted between two epitopes in a multi-epitope construct to prevent the occurrence of junctional epitopes and/or to increase the efficiency of processing. A multi-epitope construct may have one or more spacer nucleic acids. A spacer nucleic acid may flank each epitope nucleic acid in a construct, or the spacer nucleic acid to epitope nucleic acid ratio may be about 2 to 10, about 5 to 10, about 6 to 10, about 7 to 10, about 8 to 10, or about 9 to 10, where a ratio of about 8 to 10 has been determined to yield favorable results for some constructs.

The spacer nucleic acid may encode one or more amino acids. In some embodiments a spacer nucleic acid flanking a class I WIC epitope in a multi-epitope construct is between one and about eight amino acids in length, between two and eight amino acids in length, between three and eight amino acids in length, between four and eight amino acids in length, between five and eight amino acids in length, between six and eight amino acids in length, or between seven and eight amino acids in length. A spacer nucleic acid flanking a class II MHC epitope in a multi-epitope construct is in some embodiments greater than five, six, seven, or more amino acids in length, and in some embodiments greater than five or six amino acids in length.

The number of spacers in a construct, the number of amino acids encoded in a spacer polynucleotide, and the amino acid composition of a spacer can be selected to optimize epitope processing and/or minimize junctional epitopes. In some embodiments spacers are selected by concomitantly optimizing epitope processing and junctional motifs. Suitable amino acids for optimizing epitope processing are described herein. Also, suitable amino acid spacing for minimizing the number of junctional epitopes in a construct are described herein for class I and class II HLAs. For example, spacers flanking class II MHC epitopes can in some embodiments include G, P, and/or N residues as these are not generally known to be primary anchor residues (see, e.g., PCT/US00/19774). In some embodiments a spacer for flanking a class II MHC epitope includes alternating G and P residues, for example, (GP)n (SEQ ID NOs: 87-95), (PG)n (SEQ ID NOs: 96-104), (GP)nG (SEQ ID NOs: 85, 105-112), (PG)nP (SEQ ID NOs: 86, 113-120), and so forth, where n is an integer between one and ten, between two or about two, and in some embodiments a specific example of such a spacer is GPGPG (SEQ ID NO: 85) or PGPGP (SEQ ID NO: 86). In some embodiment for class I MHC epitopes, the spacer comprises one, two, three or more consecutive alanine (A) residues, optionally preceded by K, N or G.

In some multi-epitope constructs, it is sufficient that each spacer nucleic acid encode the same amino acid sequence. In multi-epitope constructs having two spacer nucleic acids encoding the same amino acid sequence, the spacer nucleic acids encoding those spacers may have the same or different nucleotide sequences, where different nucleotide sequences may decrease the likelihood of unintended recombination events when the multi-epitope construct is inserted into cells.

In other multi-epitope constructs, one or more of the spacer nucleic acids may encode different amino acid sequences. While many of the spacer nucleic acids may encode the same amino acid sequence in a multi-epitope construct, one, two, three, four, five or more spacer nucleic acids may encode different amino acid sequences, and it is possible that all of the spacer nucleic acids in a multi-epitope construct encode different amino acid sequences. Spacer nucleic acids may be optimized with respect to the epitope nucleic acids they flank by determining whether a spacer sequence will maximize epitope processing and/or minimize junctional epitopes, as described herein.

Multi-epitope constructs may be distinguished from one another according to whether the spacers in one construct optimize epitope processing or minimize junctional epitopes over another construct, and in some embodiments, constructs may be distinguished where one construct is concomitantly optimized for epitope processing and junctional epitopes over the other. Computer assisted methods and in vitro and in vivo laboratory methods for determining whether a construct is optimized for epitope processing and junctional motifs are described herein.

In some embodiments, polynucleotide constructs of the invention are provided as an expression vector comprising a nucleic acid encoding at least one pan-DR oligopeptide sequence of the invention, and optionally any or all of the sequences described herein in the context of polypeptides. Construction of such expression vectors is described, for example in PCT/US99/10646, the disclosure of which is herein incorporated by reference. The expression vectors contain at least one promoter element that is capable of expressing a transcription unit encoding the nucleic acid in the appropriate cells of an organism so that the antigen is expressed and targeted to the appropriate MHC molecule. For example, for administration to a human, a promoter element that functions in a human cell is incorporated into the expression vector.

Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994); Oligonucleotide Synthesis. A Practical Approach (Gait, ed., 1984); Kuijpers, *Nucleic Acids Research* 18(17):5197 (1994); Dueholm, *J. Org. Chem.* 59:5767-5773 (1994);

Methods in Molecular Biology, volume 20 (Agrawal, ed.); and Tijssen, Laboratory Techniques in Biochemistry and Molecular Biology—Hybridization with Nucleic Acid Probes, e.g., Part I, chapter 2 "Overview of principles of hybridization and the strategy of nucleic acid probe assays" (1993)).

The nucleic acids encoding the relevant oligopeptide sequences (e.g., epitopes) can be assembled in a construct according to standard techniques. In some embodiments, the nucleic acid sequences encoding pan-DR binding oligopeptides, and optionally multi-epitope polypeptides, are isolated using amplification techniques with oligonucleotide primers, or are chemically synthesized. Recombinant cloning techniques can also be used when appropriate. Oligonucleotide sequences are selected which either amplify (when using PCR to assemble the construct) or encode (when using synthetic oligonucleotides to assemble the construct) the desired epitopes.

Amplification techniques using primers are typically used to amplify and isolate sequences encoding the epitopes of choice from DNA or RNA (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify epitope nucleic acid sequences directly from mRNA, from cDNA, from genomic libraries or cDNA libraries. Restriction endonuclease sites can be incorporated into the primers. Multi-epitope constructs amplified by the PCR reaction can be purified from agarose gels and cloned into an appropriate vector.

Synthetic oligonucleotides can also be used to construct the polynucleotides of the invention. In some embodiments, this method is performed using a series of overlapping oligonucleotides, representing both the sense and non-sense strands of the gene. These DNA fragments are then annealed, ligated and cloned. Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.*, 12:6159-6168 (1984). Purification of oligonucleotides is by either native acrylamide gel electrophoresis or by anion-exchange HPLC as described in Pearson & Reanier, *J. Chrom.* 255:137-149 (1983).

In some embodiments, the epitopes of polynucleotide constructs of the invention are subcloned into an expression vector that contains a strong promoter to direct transcription, as well as other regulatory sequences such as enhancers and polyadenylation sites. Suitable promoters are well known in the art and described, e.g., in Sambrook et al. and Ausubel et al. Eukaryotic expression systems for mammalian cells are well known in the art and are commercially available. Such promoter elements include, for example, cytomegalovirus (CMV), Rous sarcoma virus LTR and SV40.

The expression vector typically contains a transcription unit or expression cassette that contains all the additional elements required for the expression of the polynucleotide construct in host cells. For example, an expression cassette can contain a promoter operably linked to a multi-epitope construct and signals required for efficient polyadenylation of the transcript. Additional elements of the cassette may include enhancers and introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

Selectable markers can be incorporated into the expression vectors used to express the peptides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media. In some embodiments, the vector will have one selectable marker that is functional in, e.g., *E. coli*, or other cells in which the vector is replicated prior to being introduced into the host cell. A number of selectable markers are known to those of skill in the art.

A variety of expression vectors can be used to transport the genetic information into the cell. Any of the conventional vectors used for expression in eukaryotic cells may be used. Expression vectors containing regulatory elements from eukaryotic viruses are typically used in eukaryotic expression vectors, e.g., SV40 vectors, CMV vectors, papilloma virus vectors, and vectors derived from Epstein Bar virus.

The polynucleotide constructs of the invention can be expressed from a variety of vectors including plasmid vectors as well as viral or bacterial vectors. Examples of viral expression vectors include attenuated viral hosts, such as vaccinia or fowlpox. As an example of this approach, vaccinia virus is used as a vector to express nucleotide sequences that encode the (poly)peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848.

The polynucleotides of the invention can be expressed in a variety of host cells, including *E. coli*, other bacterial hosts, yeast and insect cells, so as to obtain the protein expression products described herein. The host cells can be microorganisms, such as, for example, yeast cells, bacterial cells, or filamentous fungal cells. Examples of suitable host cells include, for example, *Pseudomonas* sp., *Escherichia* sp. (e.g., *E. coli*), *Bacillus*, among many others. Suitable yeast cells can be of any of several genera, including, for example, *Saccharomyces* (e.g., *S. cerevisiae*), and *Candida*. Suitable fungal cells are selected from *Pichia* spp., *Aspergillus* spp, and other fungi suitable for recombinant production. Suitable insect cells can be of several varieties, including, for example, S2, Sf9 and Hi-5 cells.

A wide variety of other vectors useful for therapeutic administration or immunization, e.g. adeno and adeno-associated virus vectors, retroviral vectors, non-viral vectors such as BCG (Bacille Calmette Guerin), *Salmonella typhi* vectors, detoxified anthrax toxin vectors, and the like, will be apparent to those skilled in the art. So, the invention also relates to prophylactic or therapeutic use of such vectors by means of administration to an individual in need thereof of such vectors.

Immunogenicity and antigenicity of the multi-epitope constructs are evaluated as described herein.

As set forth above, the present invention also relates to isolated polypeptides encoded by any of the polynucleotides of the invention as described herein—as such, these polypeptides are also "peptides" or "polypeptides" of the present invention.

IV. Further Antigens

As explained above, the pan-DR oligopeptides of the invention can be used to enhance a cellular or humoral immune response to a variety of antigens. Antigenic determinants from such an antigen, or the antigen as such, can be administered admixed with or linked to the pan-DR binding peptides of the present invention. For example, the antigenic determinant can be linked or mixed, or administered in series, with the helper peptides of the present invention to elicit or enhance an immune response. Essentially any antigen can be used (e.g., polysaccharides, proteins, glycoproteins, lipids, glycolipids, lipopolysaccharides and the like) in combination with the pan-DR binding oligopeptide sequences of the present invention. Protein antigens may be derived from infectious agents such as bacteria, fungi, virus, protozoans, helminths and other parasites, but they may also be disease-associated antigens, such as cancer antigens or antigens which are overexpressed or otherwise inexpedient in certain disease states. The cancer antigens listed in WO 00/20027 are all relevant protein antigens, and further antigens are those associated with inflammation (here TNF is a good example). The present invention discloses a number of TNF constructs which are all part of the invention—generally, all these constructs are also part of the invention, as are nucleic acid fragments encoding them, vectors comprising the nucleic acid fragments and host cells including the nucleic acid fragments or vectors (or being transformed with the vectors).

In some embodiments the oligopeptides of the present invention are administered alone. In some embodiments the oligopeptides of the invention are administered in conjunction with a second antigenic determinant. In some embodiments the oligopeptides of the invention are admixed with the antigenic determinant. In some embodiments the peptides of the invention are linked to the antigenic determinant. For example, protein antigens can be linked directly or indirectly to the pan-DR binding oligopeptides as fusion proteins (via peptide bonding). Antigens, including non-protein antigens, can be linked to the pan-DR oligopeptides, or polypeptides comprising the oligopeptide sequences, via other covalent conjugation methods.

In some embodiments the antigenic determinant administered with the peptides of the present invention is a protein. In some embodiments the antigenic determinant administered with the peptides of the present invention is a polysaccharide. In some embodiments the antigenic determinant administered with the peptides of the present invention is a glycoprotein. In some embodiments the antigenic determinant administered with the peptides of the present invention is a lipid. In some embodiments the antigenic determinant administered with the peptides of the present invention is a glycolipid. In some embodiments the antigenic determinant administered with the peptides of the present invention is a lipopolysaccharide.

Carbohydrate epitopes include a carbohydrate structure, but can be present as a glycoconjugate, e.g., glycoprotein, glycopeptide, glycolipid, and the like, DNA, RNA, or a polysaccharide, oligosaccharide, or monosaccharide against which an immune response is desired. The carbohydrate epitope may induce a wide range of immune responses. One of skill will recognize that various carbohydrate structures exemplified herein can be variously modified according to standard methods, without adversely affecting antigenicity. For instance, the monosaccharide units of the saccharide may be variously substituted or even replaced with small organic molecules, which serve as mimetics for the monosaccharide.

Examples of suitable antigens include those derived from bacterial surface polysaccharides which can be used in carbohydrate-based vaccines. Bacteria typically express carbohydrates on their cell surface as part of glycoproteins, glycoplipids, 0-specific side chains of lipopolysaccharides, capsular polysaccharides and the like. Exemplary bacterial strains include *Streptococcus pneumonia* (see, e.g., WO/2005/120563 and carbohydrate epitopes therein), *Neisseria meningitidis, Haemophilus influenza, Klebsiella* spp., *Pseudomonas* spp., *Salmonella* spp., *Shigella* spp., and Group B streptococci.

A number of suitable bacterial carbohydrate epitopes are described in the prior art (e.g., Sanders, et al. *Pediatr. Res.* 37:812-819 (1995); Bartoloni, et al. *Vaccine* 13:463-470 (1995); Pirofski, et al., *Infect. Immun.* 63:2906-2911 (1995) and International Publication No. WO 93/21948) and as described in, e.g., U.S. Pat. No. 6,413,935.

In general, the HLA binding epitopes disclosed in any one of the following international patent applications may according to the invention be useful and the contents of which are therefore incorporated by reference herein: WO 93/03764, WO 95/22317, WO 94/03205, WO 95/19783, WO 97/34617, WO 02/20053, WO 94/20127, WO 97/34621, WO 02/20616, WO 95/07707, WO 95/04817, WO 98/33888, WO 94/26774, WO 96/03140, WO 02/20035, WO 96/40213, WO 97/26784, WO 97/33602, WO 98/32456, WO 99/61916, WO 99/45954, WO 99/65522, WO 01/62776, WO 01/00225, WO 2004/031211, WO 99/58658, WO 2005/012502, WO 00/44775, WO 02/019986, WO 2004/031210, WO 01/21189, WO 01/24810, WO 2005/033265, WO01/42270, WO01/41788, WO01/42267, WO 01/45728, WO 0141787, WO 02/061435, WO 02/061435, WO 01/41741, WO 2004/052917, WO 01/36452, WO 03/087126, WO 01/47541, WO 02/083714, WO 01/41799, WO 2005/089164, WO 2003/040165, WO 2005/120563, WO 2004/094454, WO 2004/053086, WO 2004/089973, WO 2008/054540, WO 2008/039267, WO 99/19478, WO 92/21033, WO 94/11738, WO 93/22338, WO 95/25530, WO 95/25739, WO 2005/118626, WO 93/03753, WO 94/19011, WO 95/03777, WO 95/19783, WO 95/04542, WO 01/42270, WO 01/41788, WO 01/42267, WO 01/45728, WO 01/41787, WO 01/41741, WO 2004/052917, WO2004/094454, and WO 2004/089973.

V. Preparation of Conjugates

The pan-DR binding peptides of the invention can be linked to at least one further antigenic determinant in a variety of ways. Ionic interactions are possible through the termini or through the ϵ-amino group of lysine. Hydrogen bonding between the side groups of the residues and the antigenic determinants are also possible. In other embodiments, conformation interactions between the pan-DR binding peptide and the antigenic determinant may give rise to a stable attachment.

As noted above, antigenic determinants may be covalently linked to the pan-DR binding peptides to prepare conjugates of the invention. In some embodiments antigenic determinant/pan-DR binding peptide conjugates are linked by a spacer molecule or linker. In some embodiments, the antigenic determinant may be attached to the pan-DR binding peptide without a linker.

The spacer or linker is typically comprised of neutral molecules, such as, aliphatic carbon chains, amino acids or amino acid mimetics, which are substantially uncharged under physiological conditions and may have linear or branched side chains. A number of compositions and methods for linking various biomolecules are known to those of skill in the art. A number of methods for covalently linking a pan-DR binding peptide, for instance, to a carbohydrate epitope are possible. Methods suitable for linking pan-DR binding peptides to carbohydrate antigens are disclosed for instance in WO 93/21948.

A number of linkers are well known and are either commercially available or are described in the scientific literature. The linking molecules used in the present invention are of sufficient length to permit the two portions of the molecule to interact independently and freely with molecules exposed to them. In the case of carbohydrate epitopes, the linking molecules are typically 1-50 atoms long. In some embodiments, the linking molecules will be aryl acetylene, ethylene glycol oligomers containing 2-14 monomer units, diamines, diacids, amino acids, or combinations thereof. Other suitable linkers include lipid molecules such as ceramide and amino acid residues to which a different carbohydrate moiety is linked through the amino acid side chain.

The particular linking molecule used may be selected based upon its chemical/physical properties. The linking molecule has an appropriate functional group at each end, one group appropriate for attachment to the reactive sites on the carbohydrate portion and the other group appropriate for attachment to the amino acid/peptide portion. For example, groups appropriate for attachment to the carbohydrate portion are carboxylic acid, ester, isocyanate, alkyl halide, acyl halide and isothiocyanate. Similar groups would be useful for attachment to the amino acid portion. Appropriate selection of the functional group will depend on the nature of the reactive portion of the amino acid or peptide.

In one group of embodiments, alkyl or alkylene groups will be useful as linking groups and will have 1 to 20 carbon atoms, in some embodiments contain between 3 to 6 carbon atoms. For instance, linkers comprising polyethylene glycol and related structures can be used. The term "polyethylene glycol" is used to refer to those molecules which have repeating units of ethylene glycol, for example, hexaethylene glycol (HO—(CH$_2$CH$_2$O)$_5$—CH$_2$CH$_2$OH). When the term "polyethylene glycol" is used to refer to linking groups, it would be understood by one of skill in the art that other polyethers or polyols could be used as well (i.e, polypropylene glycol or mixtures of ethylene and propylene glycols).

In another group of embodiments, the alkyl or alkylene linking groups will be perfluorinated, rendering them less susceptible to biological degradation. see, U.S. Pat. No. 5,055,562. In some embodiments linking groups will include aminocaproic acid, 4-hydroxy butyric acid, 4-mercapto butyric acid, 3-amino-1-propanol, ethanolamine, perfluoroethanolamine, and perfluorohydroxybutyric acid. In some embodiments, the two portions are linked via a polyethylene glycol moiety.

In some embodiments, the linkers between pan-DR binding peptides and other peptides (for example but not limited to, a pan-DR binding peptide and a CTL or B-cell epitope) can be selected from Ala, Gly, or other neutral spacers of nonpolar amino acids or neutral polar amino acids. In some embodiments herein the neutral spacer is Ala. It will be understood that the optionally present spacer need not be comprised of the same residues and thus may be a hetero- or homo-oligomer. In some embodiments, exemplary spacers are homo-oligomers of Ala. When present, the spacer will usually be at least one or two residues, more usually three to six residues. In some embodiments the pan-DR binding peptide is conjugated to the CTL or antibody-inducing peptide. In some embodiments, the pan-DR binding peptide is positioned at the amino terminus. The peptides can be joined by a neutral linker, such as Ala-Ala-Ala or the like, and in some embodiments can contain a lipid residue such as palmitic acid or the like which is attached to alpha and epsilon amino groups of a Lys residue ((PAM)$_2$Lys), which is attached to the amino terminus of the peptide conjugate, typically via Ser-Ser linkage or the like.

The CTL or antibody-inducing peptide may be linked to the pan-DR binding peptide either directly or via a spacer either at the amino or carboxy terminus of the CTL peptide. The amino terminus of either the CTL or antibody inducing peptide or the pan-DR binding peptide can be acylated. In some embodiments, the CTL peptide/pan DR binding peptide conjugate can be linked to certain alkanoyl (C$_1$-C$_{20}$) lipids via one or more linking residues such as Gly, Gly-Gly, Ser, Ser-Ser as described below. In some embodiments lipid moieties include cholesterol, fatty acids, and the like.

In some embodiments the pharmaceutical compositions of the invention can contain at least one component which assists in priming CTL. Lipids have been identified as agents capable of assisting the priming CTL in vivo against viral antigens. For example but not limited to, steroids such as cholesterol, fatty acids such as palmitic acid residues can be attached to the sulfhydryl group of a cysteine residue, the alpha and epsilon amino groups of a Lys residue and then linked, e.g., via one or more linking residues such as Gly, Gly-Gly-, Ser, Ser-Ser, or the like, to an immunogenic peptide, such as a pan-DR binding peptide. In some embodiments, in place of fatty acids, long chain alkyl groups can be linked through an ether linkage to the final amino acid (e.g., a cysteine residue).

The lipidated peptide can be injected, either directly in a micellar form, incorporated into a liposome or emulsified in an adjuvant, e.g., incomplete Freund's adjuvant. In some embodiments a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine (P$_3$CSS) can be used to prime virus specific CTL when covalently attached to an appropriate peptide. See, Deres, et al., *Nature* 342:561-564 (1989). Peptides of the invention can be coupled to P$_3$CSS, for example, and the lipopeptide administered to an individual to specifically prime a CTL response to the target antigen. In some embodiments, the induction of neutralizing antibodies can also be primed with P$_3$CSS conjugated to a peptide which displays an appropriate epitope and the two compositions can be combined to more effectively elicit both humoral and cell-mediated responses to infection.

In the case of pan-DR binding peptides conjugated to carbohydrate epitopes, the lipid moieties may be linked to the opposite terminus of the peptide (e.g., carbohydrate linked to the C-terminus and lipid linked to the N-terminus). In some embodiments, both the lipid and the carbohydrate moieties may be linked to the same end of the peptide. In some embodiments, the two moieties may be linked to the same linker on the N-terminus.

VI. Methods of Stimulating an Immune Response

Polypeptide immunogens of the present invention may be expressed, concentrated and purified from expression hosts such as E. coli (or other host cells discussed above) using various methods known to one of skill in the art—alternatively, the immunogens may be prepared by liquid or solid phase peptide synthesis. Purified polypeptide or peptide immunogens can be formulated with pharmaceutically-acceptable excipients for administration into individuals, for example, to stimulate or enhance an immune response and optionally generate a protective and/or therapeutic immune response. The phrase "protective and/or therapeutic immune response" refers to a CTL and/or an HTL and/or antibody response to a disease related antigen, e.g. derived from an infectious agent, which in some way prevents or at least partially arrests disease symptoms, side effects or progression, and clears the infectious agent. In some embodiments, the polypeptides or polynucleotides of the invention are formulated into vaccines containing an immunologically effective amount of one or more of the peptides of the invention and an appropriate pharmaceutical carrier. Thus, peptides of the invention can be administered individually or in combination either in a single composition or multiple compositions.

The invention further relates to methods of administering a pharmaceutical composition comprising an expression vector of the invention or a polypeptide derived therefrom to stimulate an immune response. The expression vectors are administered by methods well known in the art as described in, for example, Donnelly et al. (*Ann. Rev. Immunol.*, 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). In one embodiment, the multi-epitope construct is administered as naked nucleic acid.

A pharmaceutical composition comprising an expression vector of the invention or a polypeptide derived therefrom can be administered to stimulate an immune response in a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An expression vector also can be administered as a topical spray, in which case one component of the composition is an appropriate propellant. The pharmaceutical composition also can be incorporated, if desired, into liposomes, microspheres or other polymer matrices as described in, for example, Felgner et al., U.S. Pat. No. 5,703,055; Gregoriadis, Liposome Technology, Vols. I to III (2nd ed. 1993). Liposomes, for example, which consist of phospholipids or other lipids, are nontoxic, physiologically acceptable and metabolizable carriers that are relatively simple to make and administer.

The expression vectors of the invention or a polypeptide derived therefrom can be delivered to the interstitial spaces of tissues of an animal body as described in, for example, Felgner et al., U.S. Pat. Nos. 5,580,859 and 5,703,055. Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Other effective methods of administering an expression vector of the invention or a polypeptide derived therefrom to stimulate an immune response include mucosal administration as described in, for example, Carson et al., U.S. Pat. No. 5,679,647. For mucosal administration, the most effective method of administration includes intranasal administration of an appropriate aerosol containing the expression vector and a pharmaceutical composition. Suppositories and topical preparations are also effective for delivery of expression vectors to mucosal tissues of genital, vaginal and ocular sites. Additionally, expression vectors can be complexed to particles and administered by a vaccine gun.

To conclude, the peptides of the present invention are useful for inducing immune responses, both with a view to prophylaxis (i.e. with a view to reducing risk of later disease) and with a view to treatment—however the peptides of the invention are also useful for inducing immune responses experimentally and with a view to inducing antibodies in animals from which antibodies and/or B lymphocytes can be isolated—this in turn allows for later production of monoclonal antibodies and antibody derivatives.

VII. Pharmaceutical Compositions

The polypeptides of the present invention, polynucleotides of the invention, and pharmaceutical and vaccine compositions thereof, can be administered to mammals, particularly humans, for prophylactic and/or therapeutic purposes. The polypeptides of the present invention can be used to elicit and/or enhance immune responses against antigens, including but not limited to, pathogen or cancer-associated or cancer-specific biomolecules (e.g., proteins, carbohydrates, etc.). Examples of diseases which can be treated using the present invention include various bacterial infections, viral infections, fungal infections, parasitic infections and cancer. As discussed above with respect to proteinaceous antigens, the cancers associated with the cancer antigens from WO 00/20027 are also examples of diseases as are various inflammatory diseases such as rheumatoid arthritis and inflammatory bowel disease.

In some therapeutic applications, the present invention is administered to an individual already suffering from cancer, inflammatory diseases or infected with the virus or microorganism of interest. Those in the incubation phase or the acute phase of the disease may be treated with the present invention separately or in conjunction with other treatments, as appropriate.

In some therapeutic applications, a composition of the present invention is administered to a patient in an amount sufficient to elicit an effective CTL response or humoral response to the microorganism or tumor antigen and to cure, or at least partially arrest, symptoms and/or complications. An amount adequate to accomplish this is defined as "therapeutically effective dose." Amounts effective for this use will depend in part on the peptide composition, the manner of administration, the stage and severity of the disease being treated, the weight and general state of health of the patient, and the judgment of the prescribing physician.

Therapeutically effective amounts of the compositions of the present invention generally range for the initial immunization that is for therapeutic or prophylactic administration, from about 1.0 μg to about 10,000 μg of polypeptide for a 70 kg patient, e.g., from about 100 to about 8000 μg, e.g., between about 200 and about 6000 μg. In some embodiments, these doses are followed by boosting dosages of from about 1.0 μg to about 3000 μg of peptide pursuant to a boosting regimen over weeks to months depending upon the patient's response and condition by measuring specific immune responses.

It should be kept in mind that the compositions of the present invention can generally be employed in serious disease states, that is, life-threatening or potentially life threatening situations. In such cases, in view of the minimization of extraneous substances and the relative nontoxic nature of the conjugates, it is possible and may be felt desirable by the treating physician to administer substantial excesses of these compositions.

In some embodiments, the present invention can be used prophylactically to prevent and/or ameliorate a particular disease, including but not limited to, bacterial infections, viral infections, fungal infections, parasitic infections and cancer. Effective amounts are as described above. Additionally, one of ordinary skill in the vaccine arts would also know how to adjust or modify prophylactic treatments, as appropriate, for example by boosting and adjusting dosages and dosing regimes.

Formulated vaccines of the invention can be combined with a pharmaceutically acceptable adjuvant. The formulated vaccines can be an aqueous solution, a suspension or an emulsion. An immunologically effective amount of each immunogen in the vaccines of the present invention is determinable by methods known in the art without undue experimentation.

The adjuvant can be any pharmaceutically acceptable adjuvant. In some embodiments the adjuvant is an alum based compound. In some embodiments the adjuvant is aluminum hydroxide. In others the adjuvant is aluminum phosphate. In some embodiments the adjuvant is EMUNADE®. EMUNADE® is an adjuvant consisting of a combination of oil, water and aluminum hydroxide. In some embodiments the adjuvant is QUIL-A, saponin vaccine adjuvant. In some embodiments the adjuvant is QUIL-A, saponin vaccine adjuvant, plus cholesterol. In some embodiments the adjuvant is an emulsion, such as but not limited to MF59 and PROVAX.

In some embodiments, ISCOM is used as an adjuvant. ISCOM is an acronym for Immune Stimulating Complex and the technology is described, e.g., in Morein et al. (*Nature* 308:457-460 (1984)). ISCOMs are lipophilic immune stimulating complexes formed as follows. The polypeptides are solubilized using standard methods, such as with a non-ionic detergent (e.g., Mega-9, Triton X-100, Octylglucoside, Digitonin, Nonidet P-40, $C_{12}E_8$, Lubrol, Tween-80). A lipid mixture is added to assist ISCOM formation. The lipid mixture can include a phosphatidyl choline and a synthetic cholesterol. In some embodiments, the mixture is first treated with non-ionic detergent at room temperature with stirring, then the lipid mixture (equal parts phosphatidyl choline and cholesterol, for example) is added and stirring continued. QUIL-A, a saponin vaccine adjuvant (a purified glycoside of saponin) is added to polypeptide composition and stirring is continued. Then the non-ionic detergent is removed (for example, by diafiltration with ammonium acetate). The matrix of the ISCOM is formed by QUIL-A, a saponin vaccine adjuvant. The morphology of an ISCOM particle, as viewed by electron microscopy, shows a typical cage like structure of approximately 35 nm in size. The ISCOM formation stage can be refined by the use of tangential flow diafiltration. ISCOMs present purified antigens in a multimeric form based on the ability of QUIL-A, a saponin vaccine adjuvant to spontaneously form micelles at a critical concentration and by a hydrophobic/hydophilic link that entrap the purified antigens. Formation of ISCOMs can be verified by electron microscopy to verify that the typical cage-like structures have been formed. The QUIL-A, a saponin vaccine adjuvant, can be added to give a final concentration of about 0.01 to 0.1%. In some embodiments, the final concentration is about 0.05%.

The invention also relates to pharmaceutical compositions comprising a pharmaceutically acceptable carrier and an expression vector of the invention or a polypeptide of the invention. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters, lipids or liposomes.

A pharmaceutically acceptable carrier can contain physiologically acceptable compounds that act, for example, to stabilize the expression vector or increase the absorption of the expression vector. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Expression vectors can additionally be complexed with other components such as peptides, polypeptides and carbohydrates. Expression vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The invention further relates to methods of administering a pharmaceutical composition comprising an expression vector of the invention or a polypeptide derived therefrom to stimulate an immune response. The expression vectors are administered by methods well known in the art as described in, for example, Donnelly et al. (*Ann. Rev. Immunol.*, 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). In one embodiment, the polynucleotides of the invention are administered as naked nucleic acid.

The compositions of the invention are also useful for induction of immune responses, e.g. in experimental animals or in animals with a view to prepare antibodies or antibody derivatives. In such compositions the requirement that the composition should be pharmaceutically acceptable is of minor importance, and it is e.g. possible to use adjuvants not considered suitable for use in humans.

PREAMBLE TO EXAMPLES

The following examples are offered to illustrate, but not to limit the claimed invention.

Proteolytic cleavage within PADRE (SEQ ID NO: 3) has been observed in PADRE-containing proteins, in particular around the two lysine residues K2 and K10 but also around W7. Cleavage within PADRE is undesirable because it, in recombinantly produced proteins, leads to heterogeneity, reduced production yield and altered stability. Even if cleavage can be successfully avoided by the use of additives during upstream and downstream processes, a resulting PADRE containing vaccine may still have poor immunogenicity and pharmacokinetics properties such as reduced half-life and improper presentation of the T helper epitope(s). Thus there is a need to remove protease sensitive amino acids/sequences from the PADRE sequence.

Provision of PADRE analogues having reduced susceptibility to protease activity will reduce the susceptibility of recombinant expression products to proteases especially in expression systems such as *E. coli* and *Drosophila* expression systems in order to avoid proteolytic cleavages within the pan DR binding peptide amino acid sequence during upstream and/or downstream processes of protein production. Further, in the event a PADRE analogue is administered to humans, either in isolated form or as part of an immunogenic polypeptide, the reduced susceptibility will entail the further advantage of improved pharmacokinetic properties (i.a. longer serum half-life) and possibly improved immunogenicity.

On this basis a number of analogues of SEQ ID NO: 3 have been prepared and subjected to the following sequence of identification steps in order to identify improved pan DR binding peptides which are less prone to proteolytic degradation:
1) Preparation of library of synthetic PADRE analogues
2) Assaying and selecting analogues from 1) for good HLA binding properties
3) Assaying and selecting analogues selected in 2) for in situ protease resistance
4) Assaying and selecting analogues selected in 3) for good immunogenic properties.

Example 1

Testing for HLA-DR Binding of PADRE Analogues

A total of 69 different PADRE analogues (SEQ ID NOs: 4-72) were synthesized by standard solid phase peptide synthesis—all these PADRE analogues are constituted by, from the N- to the C-terminus, two alanine residues followed by residues 3-15, which is an analogue of SEQ ID NO: 3 (except for SEQ ID NO: 4, which is PADRE preceded by two alanine residues). The reason for including the 2 extra N-terminal alanines was to ensure that the isolated peptides would be able to demonstrate endoprotease resistance in an in vitro assay for protease resistance, whereas the immunogenic properties of the PADRE analogues reside in the 13 C-terminal amino acids.

The peptides were tested for binding to HLA-DR according to the following procedure:
Peptide/HLA-DR Binding Assays The standard operating procedure for the class II MHC binding assay is described in Sidney et al. (1998), Current Protocols in Immunology, 18.3.1-18.3.19, 1998. Briefly, purified human class II molecules [5 to 500 nM] were incubated with various unlabeled peptide binding inhibitors and 1-10 nM $^{125}$I-radiolabeled probe peptides for 48 h in PBS containing 5% DMSO in the presence of a protease inhibitor cocktail. Final detergent concentration in the incubation mixture was 0.05% Nonidet P-40. Assays were performed at pH 7.0 with the exception of DR3, which was performed at pH 4.5, and DRw53, which was performed at pH 5.0. The pH was adjusted as described in Sette et al. (1992), J Immunol, 148:844-51.

Instead of using HPLC methodology to measure peptide binding to MHC molecules as detailed in Sidney et al., an anti-MHC class II antibody coated plate-based capture assay was utilized. This assay has been developed to use a 96-well white polystyrene microtiter plate specifically designed for high-volume, in-plate, radiometric assays. Measurement of the $^{125}$I-labeled peptide bound to MHC is accomplished using the TOPCOUNT (Perkin-Elmer Instruments) benchtop microplate scintillation and luminescence counter, which allows for a highly sensitive assay for high throughput performance.

Peptide binding inhibitors were tested at concentrations ranging from 30 µg/ml to 300 pg/ml. Utilizing commercially available curve-fitting algorithms, the data were plotted in silico and the dose yielding 50% inhibition ($IC_{50}$) was determined. In appropriate stoichiometric conditions, the $IC_{50}$ of an unlabeled test peptide to the purified DR molecule is a reasonable approximation of the affinity of interaction ($K_D$). Peptides were tested in two to four completely independent experiments.

Results

The binding affinities as indicated via the $IC_{50}$ values are listed for each peptide in FIG. 1. On the basis of these $IC_{50}$ values, it was concluded that a fraction of the analogues (38 PADRE analogues) exhibited sufficiently good HLA binding capabilities (shown in FIG. 1 by bold and underlining). Of these good binders, 10 were initially selected for further testing for protease resistance: SEQ ID NOs: 4, 10, 19, 23, 29, 38, 46, 52, 67, and 69.

It is also important to note that the inclusion of the two N-terminal alanines in SEQ ID NOs. 4-69 did not affect the HLA binding properties as evidenced by the similar binding characteristics exhibited by SEQ ID NOs: 3 and 4.

Example 2

Protease Resistance Testing of Selected PADRE Analogues

In order to test the protease resistance of selected, good binding PADRE analogues, their sequences were inserted by cloning techniques into a loop (loop EF) in human TNFα. Cell-free protein crude extract from *E. coli* expressing the modified TNFα molecules was prepared and proteolytic cleavage within the PADRE analogue sequences was analysed by SDS-PAGE followed by immunoblotting.

Full-length, membrane-bound TNFα is a 233 amino-acid long protein. The amino-terminal fragment 1-76 is absent in the 157 amino-acid long soluble form of TNFα (77-233).

The template used for the design of human TNFα vaccine candidates is the soluble form of TNFα (fragment 77-233, SEQ ID NO: 73), preceded by an N-terminal Met for expression in *E. coli*. Furthermore a point mutation was made (Y87S) in order to abolish binding of TNFα to its two receptors, thereby abolishing the cytotoxicity of the protein. Thus, the vaccine candidates are based on the 158 amino acid residue long SEQ ID NO: 74:

TNF 37.87 (SEQ ID NO: 75) is a TNF variant where PADRE is inserted between $A_{185}$ and $E_{186}$ ( . . . PEGA-EAK . . . ). Since PADRE begins with an A, the A was not duplicated, resulting in an insertion of 12 amino acids instead of 13:

```
. . . PEGA-AKFVAAWTLKAAA-EAK . . . →
PEG-A-KFVAAWTLKAAAEAK . . .
```

The TNF variants initially tested for protease resistance are thus SEQ ID NO: 75-TNF 37.87-reference protein comprising "traditional" PADRE:

```
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAKFVAAWTLKAAAEAKPWYEPIYLGGVFQLEK
GDRLSAEINRPDYLDFAESGQVYFGIIAL
``` as well as 9 PADRE analogue containing TNF variants, each similarly having the 12 C-terminal amino acid residues of SEQ ID NOs: 4, 10, 19, 23, 29, 38, 46, 52, 67, and 69, respectively, at the underlined position:

```
TNF 37.87-007 sequence:
                                        SEQ ID NO: 76
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAWFVAANTLHAAAEAKPWYEPIYLGGVFQLEK
GDRLSAEINRPDYLDFAESGQVYFGIIAL TNF 37.87-016 sequence:
                                        SEQ ID NO: 77
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAFFVAANTLKADAEAKPWYEPIYLGGVFQLEK
GDRLSAEINRPDYLDFAESGQVYFGHAL TNF 37.87-020 sequence:
                                        SEQ ID NO: 78
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAYFVAAFTLHAAAEAKPWYEPIYLGGVFQLEK
GDRLSAEINRPDYLDFAESGQVYFGIIAL TNF 37.87-026 sequence:
                                        SEQ ID NO: 79
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAHFVAANTLHAAAEAKPWYEPIYLGGVFQLEK
GDRLSAEINRPDYLDFAESGQVYFGHAL TNF 37.87-035 sequence:
                                        SEQ ID NO: 80
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAHFVAAFTLKAEAEAKPWYEPIYLGGVFQLEK
GDRLSAEINRPDYLDFAESGQVYFGIIAL TNF 37.87-043 sequence:
                                        SEQ ID NO: 81
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAEFVAAWTLHAAAEAKPWYEPIYLGGVFQLEK
GDRLSAEINRPDYLDFAESGQVYFGIIAL
```

-continued

```
TNF 37.87-049 sequence:
                                        SEQ ID NO: 82
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGANFVAAYTLHAAAEAKPWYEPIYLGGVFQLEK
GDRLSAEINRPDYLDFAESGQVYFGHAL TNF 37.87-064 sequence:
                                        SEQ ID NO: 83
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAQFVAANTLHAAAEAKPWYEPIYLGGVFQLEK
GDRLSAEINRPDYLDFAESGQVYFGHAL TNF 37.87-066 sequence:
                                        SEQ ID NO: 84
MVRSSSRTPSDKPVAHVVANPQAEGQLQWLNRRANALLANGVELRDN
QLVVPSEGLYLIYSQVLFKGQGCPSTHVLLTHTISRIAVSSQTKVNL
LSAIKSPCQRETPEGAIFVAAWTLHAAAEAKPWYEPIYLGGVFQLEK
GDRLSAEINRPDYLDFAESGQVYFGIIAL
```

In all sequences, double underlining denotes the initial methionyl and the Y87S mutation, respectively, and single underlining denotes the pan DR binding sequence inserted; bold indicates amino acid changes in the pan DR binding peptide relative to PADRE (SEQ ID NO: 3).

Cloning, Expression, Purification and Characterization of Recombinant TNFα Variants A synthetic cDNA encoding TNF (Y87S) was used as template. Oligonucleotides encoding PADRE or PADRE analogues were inserted into the template between $A_{185}$ and $E_{186}$ by PCR (cf. above). Resulting cDNAs were cloned into pET28b+(Novagen) and transformed into *E. coli* strain HMS 174. For recombinant expression, the resulting *E. coli* strains were cultured in fermentors in a defined medium at 37° C. Induction of recombinant expression was initiated by the addition of 1 mM of IPTG and temperature was lowered to 25° C. Cultures were harvested at 4, 8 or 24 h post-IPTG induction. TNFα variants were purified to >90% homogeneity by affinity chromatography using a TNFα specific monoclonal antibody as described in Nielsen et al., (2004), J Biol. Chem. 279:33593-33600. The purified TNFα variants were characterized by MALDI-TOF mass spectrometry to verify their identity and integrity.

In Situ Protease Assay: Analysis of the Protease Resistance of TNF-α Variants Using Western Blot Aliquots (1 ml) of *E. coli* cell cultures, expressing the various TNF-α variants to be tested, were centrifuged (5000 g/5 min/5° C.) and the culture medium was discarded. Cell pellets were resuspended in 1 ml of 20 mM Bis-Tris, pH 6.0. Cell disruption was achieved by sonication (4×15 sec at an amplitude of 11 μm with 20 sec pauses between each sonication round). The resulting suspensions were centrifuged (20000 g/30 min/8° C.) and the supernatants (crude extracts) were transferred to fresh tubes. Crude extracts were then analysed for protein content using a Bradford protein assay (Biorad). Equivalent amounts of proteins were loaded onto 4-12% NuPAGE gels (Novex). After SDS-PAGE, proteins were transferred onto nitrocellulose membrane by semi-dry blotting. For immunoreaction, incubation with rabbit TNFα antiserum (1 h; dilution 1:10 000) and with horse radish peroxidase-conjugated secondary antibody (Dako P448) were carried out in Tris 50 mM, NaCl 150 mM, EDTA 5 mM, Igepal 0.1%, gelatine 0.5%. Detection was with ECL™ reagents (GE Healthcare).

Results

Of the tested TNF variants, three (SEQ ID NOs: 78, 79 and 84) were shown to be protease resistant in the protease assay (data not shown), evidencing that these TNF variants are not sensitive to proteolytic cleavage inside the PADRE analogue sequence.

It was concluded that PADRE analogues defined by at least the 13 C-terminal amino acid residues of each of SEQ ID NOs: 23, 29 and 69 exhibit a desirable increased resistance towards proteolytic degradation and that proteins modified by including the 13 C-terminal amino acid residues of SEQ ID NOs: 23, 29 and 69 will exhibit superior yields when produced recombinantly (because no or only limited fragmentation of the expression product will occur), provide for a homogenous expression product and possibly provide for increased immunogenicity because of the increased biological half-life of a protease resistant immunogen.

Example 3

Immunogenicity Testing of Selected PADRE Analogues

The three protease resistant PADRE analogues identified in Example 2 were tested for their immunogenic properties. In one line of experiments, the peptides were tested as free peptides in PBMCs (peripheral blood mononuclear cells) from human donors and in two mouse strains (DR4 and bxd). In the second line of experiments, the PADRE analogues were tested in the context of the protease resistant TNF variants identified in Example 2.

Test of Peptides in Human PBMCs

Human PBMCs (peripheral blood mononuclear cells) were stimulated with the peptides with sequences identical to the 13 amino acid residues of SEQ ID NOs: 23, 29 and 69 (in the following these 3 13-mers are termed PADRE.Y2.F7.H10, PADRE H2.N7.H10 and PADRE.I2.H10, respectively). At days 1 and 4 IL-2 is added. At day 7, a portion of the cells were taken for an IFN-γ ELISPOT assay. The remaining cells were restimulated. At days 8 and 11 IL-2 was added. At day 14, CD4 cells were purified and tested in an IFN-γ ELISPOT assay.

The IFN-γ ELISPOT assay was performed essentially as described in Tangri S et al. (2005), J Immunol 174, 3187-96.

Test of Peptides in Mice

Groups of 3 individuals of each of the HLA-DR4 transgenic and bxd mouse strains were immunized with 20 μg (6 μl of 20 mg/ml peptide+294 μl PBS 1×+300 μl CFA) or 2 μg (6 μl of 2 mg/ml peptide+294 μl PBS 1×+300 μl CFA) peptide in CFA at the base of the tail. 10 to 14 days later the spleens were harvested, CD4 cells purified and tested in an IFN-γ ELISPOT assay (as described in McKinney et al. (2004), J Immunol 173, 1941-50). The peptides tested were identical to those tested in human PBMCs.

Tests of TNFα Variants in Mice

Groups of three HLA-DR4 transgenic-mice were immunized at the base of the tail with 10 μg of TNF-derived antigen/mouse in 100 μl of complete Freund's adjuvant (CFA). The animals were boosted 14 days after the first immunization using the same dose of antigen in 100 μl of IFA (incomplete Freund's adjuvant). Sera were collected 14 days after each immunization for determination of TNFα specific antibody titers. Animals were then sacrificed for IFN-γ ELISPOT assays.

Determination of TNFα Specific Antibody Titers in Mice Antisera

TNFα specific antibody titers were determined using a direct ELISA. 96-well plates (Maxisorb, Nunc) were coated with recombinant TNFα variant TNF Y87S (5 μg/ml in a carbonate buffer at pH 9.6, 100 μl/well, overnight at 4° C.). Plates were then washed three times and incubated for 2 hrs at 37° C. with 200 of blocking buffer (phosphate buffer saline containing 1% of bovine serum albumin and 0.05% of Tween 20). Plates were washed three times and pooled sera from mice immunized with human TNFα variants were titrated in six steps, using 1/10-dilution steps (starting dilution is 1/1000) in blocking buffer in a total volume of 100 μl/well samples were titrated in duplicates. Serum and control were incubated for 2 hr at 37° C. Plates were washed three times and 100 μl of a biotinylated goat anti-mouse IgG (diluted 1/10000 in blocking buffer) was transferred to each well and incubated for 1 hr at 37° C. Finally plates were washed three times and incubated for 45 min at room temperature with 100 of avidin-peroxidase complex (Vectastain Elite Vector PK-6100). Plates were washed again and developed using TMBS. The reaction was stopped after 10-20 min with 100 μl of 4N $H_2SO_4$ and $A_{450}$ values were determined using an ELISA reader. Antibody titers were defined as the antiserum dilution yielding an $A_{450}$ value of 0.5.

Results

The results from the test of the peptides in human PBMCs revealed that PADRE.Y2.F7.H10 and PADRE.I2.H10 provided for superior immune responses in the IFN-γ ELISPOT assay at both day 7 and day 14 compared to SEQ ID NO: 3, whereas PADRE.H2.N7.H10 provided for immune responses of the same order of magnitude as did SEQ ID NO: 3.

In the tests of PADRE analogue peptides in mice, all 3 tested analogues performed better than PADRE at the 20 μg dose in DR4 mice, whereas only the PADRE.I2.H10 peptide provided for improved immune responses in DR4 transgenic mice at the 2 μg dose as measured by the ELISPOT assay. In the bxd mouse model, all 3 tested PADRE analogues provided for significant immune responses compared to PADRE in the ELISPOT assay at both doses, without however providing for an improvement of the immune response compared to PADRE.

Immunizations with TNFα variants including the PADRE analogues provided for the following results:

The HTL induction in the HLA DR4 transgenic mice as measured by IFN-γ ELISPOT revealed that all TNFα-variants induced HTLs for the PADRE analogue introduced into TNFα and that PADRE.Y2.F7.H10 and PADRE.I2.H10 were superior to PADRE in this respect (where PADRE. H2.N7.H10 provided about the same HTL induction as PADRE). Further, all the variants provided for antibody titers significantly higher than those induced by wild type TNFα—the variants containing PADRE.Y2.F7.H10 and PADRE.I2.H10 were superior compared to PADRE, and again PADRE. H2.N7.H10 provided an immune response comparable to PADRE. In fact, when correlating antibody titers with HTL induction, there was a clear linear correlation.

Example 4

Selection and Test of 8 Further PADRE Analogues

Based on the identification of the pan DR binding, protease resistant and immunogenic PADRE analogues PADRE.Y2.F7.H10, PADRE.H2.N7.H10 and PADRE.I2.H10, it was decided to test further PADRE analogues identified as good binders in Example 1. The peptides tested were those having the 13 C-terminal amino acid residues from SEQ ID NOs. 15 (PADRE.F2.N7.H10), 21 (PADRE.Y2.H10), 24 (PADRE.Y2.N7.H10), 26 (PADRE.H2.H10), 47 (PADRE.E2.Y7.H10), 54 (PADRE.N2.N7.H10), 66 (PADRE.Q2.F7.H10), and 72 (PADRE.I2.N7.H10).

Three of these sequences were shown to be protease resistant according to the procedure set forth in Example 2, namely PADRE.E2.Y7.H10, PADRE.N2.N7.H10 and PADRE.Q2.N7.H10.

CONCLUSIONS

The examples described above have demonstrated the existence of a number of PADRE analogues with improved characteristics in terms of protease resistance and/or immunogenicity. It is demonstrated that careful modifications in SEQ ID NO: 3 provides for immunogens which are more stable than PADRE, both when being recombinantly expressed and when being used as in vivo immunogens.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCES

SEQ ID NO: 1:
AX$_1$FVAAX$_2$TLX$_3$AX$_4$A

SEQ ID NO: 2:
AX$_1$FVAAX$_2$TLHAAA

SEQ ID NO: 3:
AKFVAAWTLKAAA

SEQ ID NO: 4:
AAAKFVAAWTLKAAA

SEQ ID NO: 5:
AAAWFVAAWTLKAAA

SEQ ID NO: 6:
AAAKFVAAWTLHAAA

SEQ ID NO: 7:
AAAWFVAAWTLHAAA

SEQ ID NO: 8:
AAAWFVAAYTLHAAA

SEQ ID NO: 9:
AAAWFVAAFTLHAAA

SEQ ID NO: 10:
AAAWFVAANTLHAAA

SEQ ID NO: 11:
AAAFFVAAWTLKAAA

SEQ ID NO: 12:
AAAFFVAAWTLHAAA

SEQ ID NO: 13:
AAAFFVAAYTLHAAA

SEQ ID NO: 14:
AAAFFVAAFTLHAAA

SEQ ID NO: 15:
AAAFFVAANTLHAAA

SEQ ID NO: 16:
AAAFFVAAWTLKADA

SEQ ID NO: 17:
AAAFFVAAYTLKADA

SEQ ID NO: 18:
AAAFFVAAFTLKADA

SEQ ID NO: 19:
AAAFFVAANTLKADA

SEQ ID NO: 20:
AAAYFVAAWTLKAAA

SEQ ID NO: 21:
AAAYFVAAWTLHAAA

SEQ ID NO: 22:
AAAYFVAAYTLHAAA

SEQ ID NO: 23:
AAAYFVAAFTLHAAA

SEQ ID NO: 24:
AAAYFVAANTLHAAA

SEQ ID NO: 25:
AAAHFVAAWTLKAAA

SEQ ID NO: 26:
AAAHFVAAWTLHAAA

SEQ ID NO: 27:
AAAHFVAAYTLHAAA

SEQ ID NO: 28:
AAAHFVAAFTLHAAA

SEQ ID NO: 29:
AAAHFVAANTLHAAA

SEQ ID NO: 30:
AAAKFVAAWTLKADA

SEQ ID NO: 31:
AAAHFVAAWTLKADA

SEQ ID NO: 32:
AAAHFVAAYTLKADA

SEQ ID NO: 33:
AAAHFVAAFTLKADA

SEQ ID NO: 34:
AAAHFVAANTLKADA

SEQ ID NO: 35:
AAAKFVAAWTLKAEA

SEQ ID NO: 36:
AAAHFVAAWTLKAEA

SEQ ID NO: 37:
AAAHFVAAYTLKAEA

SEQ ID NO: 38:
AAAHFVAAFTLKAEA

SEQ ID NO: 39:
AAAHFVAANTLKAEA

SEQ ID NO: 40:
AAADFVAAWTLKAAA

SEQ ID NO: 41:
AAADFVAAWTLHAAA

SEQ ID NO: 42:
AAADFVAAYTLHAAA

SEQ ID NO: 43:
AAADFVAAFTLHAAA

SEQ ID NO: 44:
AAADFVAANTLHAAA

SEQ ID NO: 45:
AAAEFVAAWTLKAAA

SEQ ID NO: 46:
AAAEFVAAWTLHAAA

SEQ ID NO: 47:
AAAEFVAAYTLHAAA

SEQ ID NO: 48:
AAAEFVAAFTLHAAA

SEQ ID NO: 49:
AAAEFVAANTLHAAA

SEQ ID NO: 50:
AAANFVAAWTLKAAA

SEQ ID NO: 51:
AAANFVAAWTLHAAA

SEQ ID NO: 52:
AAANFVAAYTLHAAA

SEQ ID NO: 53:
AAANFVAAFTLHAAA

SEQ ID NO: 54:
AAANFVAANTLHAAA

SEQ ID NO: 55:
AAANFVAAWTLKADA

SEQ ID NO: 56:
AAANFVAAYTLKADA

SEQ ID NO: 57:
AAANFVAAFTLKADA

SEQ ID NO: 58:
AAANFVAANTLKADA

SEQ ID NO: 59:
AAANFVAAWTLKAEA

SEQ ID NO: 60:
AAANFVAAYTLKAEA

SEQ ID NO: 61:
AAANFVAAFTLKAEA

SEQ ID NO: 62:
AAANFVAANTLKAEA

SEQ ID NO: 63:
AAAQFVAAWTLKAAA

SEQ ID NO: 64:
AAAQFVAAWTLHAAA

SEQ ID NO: 65:
AAAQFVAAYTLHAAA

SEQ ID NO: 66:
AAAQFVAAFTLHAAA

SEQ ID NO: 67:
AAAQFVAANTLHAAA

SEQ ID NO: 68:
AAAIFVAAWTLKAAA

SEQ ID NO: 69:
AAAIFVAAWTLHAAA

SEQ ID NO: 70:
AAAIFVAAYTLHAAA

SEQ ID NO: 71:
AAAIFVAAFTLHAAA

SEQ ID NO: 72:
AAAIFVAANTLHAAA

SEQ ID NO: 73:
VRSSSRTPSDKPVAHVVANPQAEGQLQWLNRRANALLANGVELRDNQ

LVVPSEGLYLIYSQVLFKGQGCPSTHVLLTHTISRIAVSYQTKVNLL

SAIKSPCQRETPEGAEAKPWYEPIYLGGVFQLEKGDRLSAEINRPDY

LDFAESGQVYFGIIAL

SEQ ID NO: 74:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAEAKPWYEPIYLGGVFQLEKGDRLSAEINRPD

YLDFAESGQVYFGIIAL

SEQ ID NO: 75:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAKFVAAWTLKAAAEAKPWYEPIYLGGVFQLEK

GDRLSAEINRPDYLDFAESGQVYFGIIAL

SEQ ID NO: 76:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAWFVAANTLHAAAEAKPWYEPIYLGGVFQLEK

GDRLSAEINRPDYLDFAESGQVYFGIIAL

SEQ ID NO: 77:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAFFVAANTLKADAEAKPWYEPIYLGGVFQLEK

GDRLSAEINRPDYLDFAESGQVYFGIIAL

SEQ ID NO: 78:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAYFVAAFTLHAAAEAKPWYEPIYLGGVFQLEK

GDRLSAEINRPDYLDFAESGQVYFGIIAL

SEQ ID NO: 79:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAHFVAANTLHAAAEAKPWYEPIYLGGVFQLEK

GDRLSAEINRPDYLDFAESGQVYFGIIAL

-continued

SEQ ID NO: 80:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAHFVAAFTLKAEAEAKPWYEPIYLGGVFQLEK

GDRLSAEINRPDYLDFAESGQVYFGIIAL

SEQ ID NO: 81:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAEFVAAWTLHAAAEAKPWYEPIYLGGVFQLEK

GDRLSAEINRPDYLDFAESGQVYFGIIAL

SEQ ID NO: 82:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGANFVAAYTLHAAAEAKPWYEPIYLGGVFQLEK

GDRLSAEINRPDYLDFAESGQVYFGIIAL

SEQ ID NO: 83:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

SAIKSPCQRETPEGAQFVAANTLHAAAEAKPWYEPIYLGGVFQLEKG

DRLSAEINRPDYLDFAESGQVYFGIIAL

SEQ ID NO: 84:
MVRSSSRTPSDKPVAHVVANPQAEGQLQWLNRRANALLANGVELRDN

QLVVPSEGLYLIYSQVLFKGQGCPSTHVLLTHTISRIAVSSQTKVNL

LSAIKSPCQRETPEGAIFVAAWTLHAAAEAKPWYEPIYLGGVFQLEK

GDRLSAEINRPDYLDFAESGQVYFGIIAL

What is claimed is:

1. An isolated oligopeptide that can bind to at least three different HLA-DR alleles with an $IC_{50}$ value of less than 100 nM, wherein the oligopeptide sequence comprises $AX_1FVAAX_2TLX_3AX_4A$ (SEQ ID NO: 1), wherein
$X_1$ is H;
X2 is selected from the group consisting of F, N, Y and W; and
$X_3$ is H; and
$X_4$ is selected from the group consisting of A, D and E.

2. The isolated oligopeptide of claim 1, wherein
$X_1$ is H;
$X_2$ is selected from the group consisting of F, N, Y and W; and
$X_3$ is H; and
$X_4$ is A.

3. The isolated oligopeptide of claim 1, having the amino acid sequence identical to the 13 amino acid residue C-terminal fragment of SEQ ID NO: 29.

4. An isolated polypeptide comprising an oligopeptide sequence that can bind to at least three different HLA-DR alleles with an $IC_{50}$ value of less than 100 nM, wherein the oligopeptide sequence comprises $AX_1FVAAX_2TLX_3AX_4A$ (SEQ ID NO:1), wherein
$X_1$ is H;
$X_2$ is selected from the group consisting of F, N, Y, and W; and
$X_3$ is H; and
$X_4$ is selected from the group consisting of A, D and E.

5. The isolated polypeptide of claim 4, wherein
X1 is H;
X2 is selected from the group consisting of F, N, Y and W; and
X3 is H; and
X4 is A.

6. The isolated polypeptide of claim 4, wherein the oligopeptide consists of the amino acid sequence identical to the 13 amino acid residue C-terminal fragment of the oligopeptide consisting of SEQ ID NO: 29.

7. The isolated polypeptide of claim 4, wherein the polypeptide, in addition to the oligopeptide, includes a majority of a native polypeptide sequence.

8. The isolated polypeptide of claim 7, wherein the native polypeptide sequence is from human TNFα.

9. A composition comprising a polypeptide according to claim 4 and an antigen.

10. The composition of claim 9, wherein the antigen is a second polypeptide.

11. A composition comprising a physiologically acceptable excipient and a polypeptide as defined in claim 4.

12. The composition of claim 11, further comprising an antigen.

* * * * *

SEQUENCE LISTING

```
<160> NUMBER OF SEQ ID NOS: 120

<210> SEQ ID NO 1
<211> LENGTH: 13
<212> TYPE: PRT
<213> ORGANISM: Artificial Sequence
<220> FEATURE:
<223> OTHER INFORMATION: Synthetic pan-DR binding peptide
<220> FEATURE:
<221> NAME/KEY: MISC_FEATURE
<222> LOCATION: (2)..(2)
<223> OTHER INFORMATION: Xaa can be Trp, Phe, Tyr, His, Asp, Glu, Asn,
      Gln, Ile, or Lys
<220> FEATURE:
<221> NAME/KEY: MISC_FEATURE
<222> LOCATION: (7)..(7)
<223> OTHER INFORMATION: Xaa can be Phe, Asn, Tyr or Lys
<220> FEATURE:
<221> NAME/KEY: MISC_FEATURE
<222> LOCATION: (10)..(10)
<223> OTHER INFORMATION: Xaa can be His or Lys
<220> FEATURE:
<221> NAME/KEY: MISC_FEATURE
<222> LOCATION: (12)..(12)
<223> OTHER INFORMATION: Xaa can be Ala, Asp or Glu

<400> SEQUENCE: 1

Ala Xaa Phe Val Ala Ala Xaa Thr Leu Xaa Ala Xaa Ala
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic pan-DR binding peptide
<220> FEATURE:
<221> NAME/KEY: MISC_FEATURE
<222> LOCATION: (2)..(2)
<223> OTHER INFORMATION: Xaa can be Tyr, His, Ile, Glu, Asn, Gln and Lys
<220> FEATURE:
<221> NAME/KEY: MISC_FEATURE
<222> LOCATION: (7)..(7)
<223> OTHER INFORMATION: Xaa can be Phe, Asn, Tyr or Trp

<400> SEQUENCE: 2

Ala Xaa Phe Val Ala Ala Xaa Thr Leu His Ala Ala Ala
1               5                   10
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic pan-DR binding peptide

<400> SEQUENCE: 3

Ala Lys Phe Val Ala Ala Trp Thr Leu Lys Ala Ala Ala
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 4

Ala Ala Ala Lys Phe Val Ala Ala Trp Thr Leu Lys Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 5

Ala Ala Ala Trp Phe Val Ala Ala Trp Thr Leu Lys Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 6

Ala Ala Ala Lys Phe Val Ala Ala Trp Thr Leu His Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 7

Ala Ala Ala Trp Phe Val Ala Ala Trp Thr Leu His Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 8

Ala Ala Ala Trp Phe Val Ala Ala Tyr Thr Leu His Ala Ala Ala
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 9

Ala Ala Ala Trp Phe Val Ala Ala Phe Thr Leu His Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 10

Ala Ala Ala Trp Phe Val Ala Ala Asn Thr Leu His Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 11

Ala Ala Ala Phe Phe Val Ala Ala Trp Thr Leu Lys Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 12

Ala Ala Ala Phe Phe Val Ala Ala Trp Thr Leu His Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 13

Ala Ala Ala Phe Phe Val Ala Ala Tyr Thr Leu His Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 14

Ala Ala Ala Phe Phe Val Ala Ala Phe Thr Leu His Ala Ala Ala
1               5                   10                  15
```

```
<210> SEQ ID NO 15
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 15

Ala Ala Ala Phe Phe Val Ala Ala Asn Thr Leu His Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 16

Ala Ala Ala Phe Phe Val Ala Ala Trp Thr Leu Lys Ala Asp Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 17

Ala Ala Ala Phe Phe Val Ala Ala Tyr Thr Leu Lys Ala Asp Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 18

Ala Ala Ala Phe Phe Val Ala Ala Phe Thr Leu Lys Ala Asp Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 19

Ala Ala Ala Phe Phe Val Ala Ala Asn Thr Leu Lys Ala Asp Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 20

Ala Ala Ala Tyr Phe Val Ala Ala Trp Thr Leu Lys Ala Ala Ala
1               5                   10                  15
```

```
<210> SEQ ID NO 21
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 21

Ala Ala Ala Tyr Phe Val Ala Ala Trp Thr Leu His Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 22

Ala Ala Ala Tyr Phe Val Ala Ala Tyr Thr Leu His Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 23

Ala Ala Ala Tyr Phe Val Ala Ala Phe Thr Leu His Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 24

Ala Ala Ala Tyr Phe Val Ala Ala Asn Thr Leu His Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 25

Ala Ala Ala His Phe Val Ala Ala Trp Thr Leu Lys Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 26

Ala Ala Ala His Phe Val Ala Ala Trp Thr Leu His Ala Ala Ala
1               5                   10                  15
```

```
<210> SEQ ID NO 27
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 27

Ala Ala Ala His Phe Val Ala Ala Tyr Thr Leu His Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 28

Ala Ala Ala His Phe Val Ala Ala Phe Thr Leu His Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 29

Ala Ala Ala His Phe Val Ala Ala Asn Thr Leu His Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 30

Ala Ala Ala Lys Phe Val Ala Ala Trp Thr Leu Lys Ala Asp Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 31

Ala Ala Ala His Phe Val Ala Ala Trp Thr Leu Lys Ala Asp Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 32

Ala Ala Ala His Phe Val Ala Ala Tyr Thr Leu Lys Ala Asp Ala
1               5                   10                  15
```

```
<210> SEQ ID NO 33
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 33

Ala Ala Ala His Phe Val Ala Ala Phe Thr Leu Lys Ala Asp Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 34

Ala Ala Ala His Phe Val Ala Ala Asn Thr Leu Lys Ala Asp Ala
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 35

Ala Ala Ala Lys Phe Val Ala Ala Trp Thr Leu Lys Ala Glu Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 36

Ala Ala Ala His Phe Val Ala Ala Trp Thr Leu Lys Ala Glu Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 37

Ala Ala Ala His Phe Val Ala Ala Tyr Thr Leu Lys Ala Glu Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 38

Ala Ala Ala His Phe Val Ala Ala Phe Thr Leu Lys Ala Glu Ala
1               5                   10                  15
```

```
<210> SEQ ID NO 39
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 39

Ala Ala Ala His Phe Val Ala Ala Asn Thr Leu Lys Ala Glu Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 40

Ala Ala Ala Asp Phe Val Ala Ala Trp Thr Leu Lys Ala Ala Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 41

Ala Ala Ala Asp Phe Val Ala Ala Trp Thr Leu His Ala Ala Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 42

Ala Ala Ala Asp Phe Val Ala Ala Tyr Thr Leu His Ala Ala Ala
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 43

Ala Ala Ala Asp Phe Val Ala Ala Phe Thr Leu His Ala Ala Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 44

Ala Ala Ala Asp Phe Val Ala Ala Asn Thr Leu His Ala Ala Ala
1               5                   10                  15
```

```
<210> SEQ ID NO 45
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 45

Ala Ala Ala Glu Phe Val Ala Ala Trp Thr Leu Lys Ala Ala Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 46

Ala Ala Ala Glu Phe Val Ala Ala Trp Thr Leu His Ala Ala Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 47

Ala Ala Ala Glu Phe Val Ala Ala Tyr Thr Leu His Ala Ala Ala
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 48

Ala Ala Ala Glu Phe Val Ala Ala Phe Thr Leu His Ala Ala Ala
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 49

Ala Ala Ala Glu Phe Val Ala Ala Asn Thr Leu His Ala Ala Ala
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 50

Ala Ala Ala Asn Phe Val Ala Ala Trp Thr Leu Lys Ala Ala Ala
1               5                   10                  15
```

<210> SEQ ID NO 51
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 51

Ala Ala Ala Asn Phe Val Ala Ala Trp Thr Leu His Ala Ala Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 52

Ala Ala Ala Asn Phe Val Ala Ala Tyr Thr Leu His Ala Ala Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 53

Ala Ala Ala Asn Phe Val Ala Ala Phe Thr Leu His Ala Ala Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 54

Ala Ala Ala Asn Phe Val Ala Ala Asn Thr Leu His Ala Ala Ala
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 55

Ala Ala Ala Asn Phe Val Ala Ala Trp Thr Leu Lys Ala Asp Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 56

Ala Ala Ala Asn Phe Val Ala Ala Tyr Thr Leu Lys Ala Asp Ala
1               5                   10                  15

```
<210> SEQ ID NO 57
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 57

Ala Ala Ala Asn Phe Val Ala Ala Phe Thr Leu Lys Ala Asp Ala
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 58

Ala Ala Ala Asn Phe Val Ala Ala Asn Thr Leu Lys Ala Asp Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 59

Ala Ala Ala Asn Phe Val Ala Ala Trp Thr Leu Lys Ala Glu Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 60

Ala Ala Ala Asn Phe Val Ala Ala Tyr Thr Leu Lys Ala Glu Ala
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 61

Ala Ala Ala Asn Phe Val Ala Ala Phe Thr Leu Lys Ala Glu Ala
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 62

Ala Ala Ala Asn Phe Val Ala Ala Asn Thr Leu Lys Ala Glu Ala
1               5                   10                  15
```

```
<210> SEQ ID NO 63
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 63

Ala Ala Ala Gln Phe Val Ala Ala Trp Thr Leu Lys Ala Ala Ala
1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 64

Ala Ala Ala Gln Phe Val Ala Ala Trp Thr Leu His Ala Ala Ala
1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 65

Ala Ala Ala Gln Phe Val Ala Ala Tyr Thr Leu His Ala Ala Ala
1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 66

Ala Ala Ala Gln Phe Val Ala Ala Phe Thr Leu His Ala Ala Ala
1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 67

Ala Ala Ala Gln Phe Val Ala Ala Asn Thr Leu His Ala Ala Ala
1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 68

Ala Ala Ala Ile Phe Val Ala Ala Trp Thr Leu Lys Ala Ala Ala
1               5                  10                  15
```

```
<210> SEQ ID NO 69
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 69

Ala Ala Ala Ile Phe Val Ala Ala Trp Thr Leu His Ala Ala Ala
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 70

Ala Ala Ala Ile Phe Val Ala Ala Tyr Thr Leu His Ala Ala Ala
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 71

Ala Ala Ala Ile Phe Val Ala Ala Phe Thr Leu His Ala Ala Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic pan-DR binding peptide

<400> SEQUENCE: 72

Ala Ala Ala Ile Phe Val Ala Ala Asn Thr Leu His Ala Ala Ala
1               5                   10                  15

<210> SEQ ID NO 73
<211> LENGTH: 157
<212> TYPE: PRT
<213> ORGANISM: Artificial Sequence
<220> FEATURE:
<223> OTHER INFORMATION: Synthetic TNF variant

<400> SEQUENCE: 73

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95
```

```
Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 74
<211> LENGTH: 158
<212> TYPE: PRT
<213> ORGANISM: Artificial Sequence
<220> FEATURE:
<223> OTHER INFORMATION: Synthetic TNF variant

<400> SEQUENCE: 74

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

<210> SEQ ID NO 75
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 75

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80
```

```
Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Lys Phe
            100                 105                 110

Val Ala Ala Trp Thr Leu Lys Ala Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 76
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 76

Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Trp Phe
            100                 105                 110

Val Ala Ala Asn Thr Leu His Ala Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 77
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 77

Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30
```

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
 50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Phe Phe
            100                 105                 110

Val Ala Ala Asn Thr Leu Lys Ala Asp Ala Glu Ala Lys Pro Trp Tyr
            115                 120                 125

Glu Pro Ile Tyr Leu Gly Gly Val Phe Gln Leu Glu Lys Gly Asp Arg
            130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
            165                 170

<210> SEQ ID NO 78
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 78

Met Val Arg Ser Ser Ser Arg Thr Pro Ser Asp Lys Pro Val Ala His
 1               5                  10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
 50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Tyr Phe
            100                 105                 110

Val Ala Ala Phe Thr Leu His Ala Ala Glu Ala Lys Pro Trp Tyr
            115                 120                 125

Glu Pro Ile Tyr Leu Gly Gly Val Phe Gln Leu Glu Lys Gly Asp Arg
            130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
            165                 170

<210> SEQ ID NO 79
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 79

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala His Phe
            100                 105                 110

Val Ala Ala Asn Thr Leu His Ala Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 80
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 80

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala His Phe
            100                 105                 110

Val Ala Ala Phe Thr Leu Lys Ala Glu Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

```
<210> SEQ ID NO 81
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 81
```

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Glu Phe
            100                 105                 110

Val Ala Ala Trp Thr Leu His Ala Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

```
<210> SEQ ID NO 82
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 82
```

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Asn Phe
            100                 105                 110

Val Ala Ala Tyr Thr Leu His Ala Ala Glu Ala Lys Pro Trp Tyr
        115                 120                 125

```
Glu Pro Ile Tyr Leu Gly Gly Val Phe Gln Leu Glu Lys Gly Asp Arg
        130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 83
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 83

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Ser Gln Thr Lys Val Asn Leu Leu Ser
                85                  90                  95

Ala Ile Lys Ser Pro Cys Gln Arg Glu Thr Pro Glu Gly Ala Gln Phe
            100                 105                 110

Val Ala Ala Asn Thr Leu His Ala Ala Glu Ala Lys Pro Trp Tyr
        115                 120                 125

Glu Pro Ile Tyr Leu Gly Gly Val Phe Gln Leu Glu Lys Gly Asp Arg
        130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 84
<211> LENGTH: 170
<212> TYPE: PRT
<213> ORGANISM: Artificial Sequence
<220> FEATURE:
<223> OTHER INFORMATION: Synthetic TNF variant incorporating pan-DR
      binding peptide

<400> SEQUENCE: 84

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80
```

```
Ile Ser Arg Ile Ala Val Ser Gln Thr Lys Val Asn Leu Leu Ser
            85                  90                  95

Ala Ile Lys Ser Pro Cys Gln Arg Glu Thr Pro Glu Gly Ala Ile Phe
        100                 105                 110

Val Ala Ala Trp Thr Leu His Ala Ala Ala Glu Ala Lys Pro Trp Tyr
        115                 120                 125

Glu Pro Ile Tyr Leu Gly Gly Val Phe Gln Leu Glu Lys Gly Asp Arg
        130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 85
<211> LENGTH: 5
<212> TYPE: PRT
<213> ORGANISM: Artificial Sequence
<220> FEATURE:
<223> OTHER INFORMATION: spacer

<400> SEQUENCE: 85

Gly Pro Gly Pro Gly
1               5

<210> SEQ ID NO 86
<211> LENGTH: 5
<212> TYPE: PRT
<213> ORGANISM: Artificial Sequence
<220> FEATURE:
<223> OTHER INFORMATION: spacer

<400> SEQUENCE: 86

Pro Gly Pro Gly Pro
1               5

<210> SEQ ID NO 87
<211> LENGTH: 4
<212> TYPE: PRT
<213> ORGANISM: Artificial Sequence
<220> FEATURE:
<223> OTHER INFORMATION: spacer

<400> SEQUENCE: 87

Gly Pro Gly Pro
1

<210> SEQ ID NO 88
<211> LENGTH: 6
<212> TYPE: PRT
<213> ORGANISM: Artificial Sequence
<220> FEATURE:
<223> OTHER INFORMATION: spacer

<400> SEQUENCE: 88

Gly Pro Gly Pro Gly Pro
1               5

<210> SEQ ID NO 89
<211> LENGTH: 8
<212> TYPE: PRT
<213> ORGANISM: Artificial Sequence
<220> FEATURE:
<223> OTHER INFORMATION: spacer
```

```
<400> SEQUENCE: 89

Gly Pro Gly Pro Gly Pro Gly Pro
1               5

<210> SEQ ID NO 90
<211> LENGTH: 10
<212> TYPE: PRT
<213> ORGANISM: Artificial Sequence
<220> FEATURE:
<223> OTHER INFORMATION: spacer

<400> SEQUENCE: 90

Gly Pro Gly Pro Gly Pro Gly Pro Gly Pro
1               5                  10

<210> SEQ ID NO 91
<211> LENGTH: 12
<212> TYPE: PRT
<213> ORGANISM: Artificial Sequence
<220> FEATURE:
<223> OTHER INFORMATION: spacer

<400> SEQUENCE: 91

Gly Pro Gly Pro Gly Pro Gly Pro Gly Pro Gly Pro
1               5                  10

<210> SEQ ID NO 92
<211> LENGTH: 14
<212> TYPE: PRT
<213> ORGANISM: Artificial Sequence
<220> FEATURE:
<223> OTHER INFORMATION: spacer

<400> SEQUENCE: 92

Gly Pro Gly Pro Gly Pro Gly Pro Gly Pro Gly Pro Gly Pro
1               5                  10

<210> SEQ ID NO 93
<211> LENGTH: 16
<212> TYPE: PRT
<213> ORGANISM: Artificial Sequence
<220> FEATURE:
<223> OTHER INFORMATION: spacer

<400> SEQUENCE: 93

Gly Pro Gly Pro Gly Pro Gly Pro Gly Pro Gly Pro Gly Pro Gly Pro
1               5                  10                  15

<210> SEQ ID NO 94
<211> LENGTH: 18
<212> TYPE: PRT
<213> ORGANISM: Artificial Sequence
<220> FEATURE:
<223> OTHER INFORMATION: spacer

<400> SEQUENCE: 94

Gly Pro Gly Pro Gly Pro Gly Pro Gly Pro Gly Pro Gly Pro Gly Pro
1               5                  10                  15

Gly Pro

<210> SEQ ID NO 95
<211> LENGTH: 20
<212> TYPE: PRT
<213> ORGANISM: Artificial Sequence
<220> FEATURE:
<223> OTHER INFORMATION: spacer
```

```
<400> SEQUENCE: 95

Gly Pro Gly Pro Gly Pro Gly Pro Gly Pro Gly Pro Gly Pro
1               5                   10                  15

Gly Pro Gly Pro
            20

<210> SEQ ID NO 96
<211> LENGTH: 4
<212> TYPE: PRT
<213> ORGANISM: Artificial Sequence
<220> FEATURE:
<223> OTHER INFORMATION: spacer

<400> SEQUENCE: 96

Pro Gly Pro Gly
1

<210> SEQ ID NO 97
<211> LENGTH: 6
<212> TYPE: PRT
<213> ORGANISM: Artificial Sequence
<220> FEATURE:
<223> OTHER INFORMATION: spacer

<400> SEQUENCE: 97

Pro Gly Pro Gly Pro Gly
1               5

<210> SEQ ID NO 98
<211> LENGTH: 8
<212> TYPE: PRT
<213> ORGANISM: Artificial Sequence
<220> FEATURE:
<223> OTHER INFORMATION: spacer

<400> SEQUENCE: 98

Pro Gly Pro Gly Pro Gly Pro Gly
1               5

<210> SEQ ID NO 99
<211> LENGTH: 10
<212> TYPE: PRT
<213> ORGANISM: Artificial Sequence
<220> FEATURE:
<223> OTHER INFORMATION: spacer

<400> SEQUENCE: 99

Pro Gly Pro Gly Pro Gly Pro Gly Pro Gly
1               5                   10

<210> SEQ ID NO 100
<211> LENGTH: 12
<212> TYPE: PRT
<213> ORGANISM: Artificial Sequence
<220> FEATURE:
<223> OTHER INFORMATION: spacer

<400> SEQUENCE: 100

Pro Gly Pro Gly Pro Gly Pro Gly Pro Gly Pro Gly
1               5                   10

<210> SEQ ID NO 101
<211> LENGTH: 14
<212> TYPE: PRT
<213> ORGANISM: Artificial Sequence
```

```
<220> FEATURE:
<223> OTHER INFORMATION: spacer

<400> SEQUENCE: 101

Pro Gly Pro Gly Pro Gly Pro Gly Pro Gly Pro Gly Pro Gly
1               5                   10

<210> SEQ ID NO 102
<211> LENGTH: 16
<212> TYPE: PRT
<213> ORGANISM: Artificial Sequence
<220> FEATURE:
<223> OTHER INFORMATION: spacer

<400> SEQUENCE: 102

Pro Gly Pro Gly Pro Gly Pro Gly Pro Gly Pro Gly Pro Gly Pro Gly
1               5                   10                  15

<210> SEQ ID NO 103
<211> LENGTH: 18
<212> TYPE: PRT
<213> ORGANISM: Artificial Sequence
<220> FEATURE:
<223> OTHER INFORMATION: spacer

<400> SEQUENCE: 103

Pro Gly Pro Gly Pro Gly Pro Gly Pro Gly Pro Gly Pro Gly Pro Gly
1               5                   10                  15

Pro Gly

<210> SEQ ID NO 104
<211> LENGTH: 20
<212> TYPE: PRT
<213> ORGANISM: Artificial Sequence
<220> FEATURE:
<223> OTHER INFORMATION: spacer

<400> SEQUENCE: 104

Pro Gly Pro Gly Pro Gly Pro Gly Pro Gly Pro Gly Pro Gly Pro Gly
1               5                   10                  15

Pro Gly Pro Gly
        20

<210> SEQ ID NO 105
<211> LENGTH: 7
<212> TYPE: PRT
<213> ORGANISM: Artificial Sequence
<220> FEATURE:
<223> OTHER INFORMATION: spacer

<400> SEQUENCE: 105

Gly Pro Gly Pro Gly Pro Gly
1               5

<210> SEQ ID NO 106
<211> LENGTH: 9
<212> TYPE: PRT
<213> ORGANISM: Artificial Sequence
<220> FEATURE:
<223> OTHER INFORMATION: spacer

<400> SEQUENCE: 106

Gly Pro Gly Pro Gly Pro Gly Pro Gly
1               5
```

```
<210> SEQ ID NO 107
<211> LENGTH: 11
<212> TYPE: PRT
<213> ORGANISM: Artificial Sequence
<220> FEATURE:
<223> OTHER INFORMATION: spacer

<400> SEQUENCE: 107

Gly Pro Gly Pro Gly Pro Gly Pro Gly Pro Gly
1               5                   10

<210> SEQ ID NO 108
<211> LENGTH: 13
<212> TYPE: PRT
<213> ORGANISM: Artificial Sequence
<220> FEATURE:
<223> OTHER INFORMATION: spacer

<400> SEQUENCE: 108

Gly Pro Gly Pro Gly Pro Gly Pro Gly Pro Gly Pro Gly
1               5                   10

<210> SEQ ID NO 109
<211> LENGTH: 15
<212> TYPE: PRT
<213> ORGANISM: Artificial Sequence
<220> FEATURE:
<223> OTHER INFORMATION: spacer

<400> SEQUENCE: 109

Gly Pro Gly Pro Gly Pro Gly Pro Gly Pro Gly Pro Gly Pro Gly
1               5                   10                  15

<210> SEQ ID NO 110
<211> LENGTH: 17
<212> TYPE: PRT
<213> ORGANISM: Artificial Sequence
<220> FEATURE:
<223> OTHER INFORMATION: spacer

<400> SEQUENCE: 110

Gly Pro Gly Pro Gly Pro Gly Pro Gly Pro Gly Pro Gly Pro Gly Pro
1               5                   10                  15

Gly

<210> SEQ ID NO 111
<211> LENGTH: 19
<212> TYPE: PRT
<213> ORGANISM: Artificial Sequence
<220> FEATURE:
<223> OTHER INFORMATION: spacer

<400> SEQUENCE: 111

Gly Pro Gly Pro Gly Pro Gly Pro Gly Pro Gly Pro Gly Pro Gly Pro
1               5                   10                  15

Gly Pro Gly

<210> SEQ ID NO 112
<211> LENGTH: 21
<212> TYPE: PRT
<213> ORGANISM: Artificial Sequence
<220> FEATURE:
<223> OTHER INFORMATION: spacer
```

```
<400> SEQUENCE: 112

Gly Pro Gly Pro Gly Pro Gly Pro Gly Pro Gly Pro Gly Pro
1               5                   10                  15

Gly Pro Gly Pro Gly
            20

<210> SEQ ID NO 113
<211> LENGTH: 7
<212> TYPE: PRT
<213> ORGANISM: Artificial Sequence
<220> FEATURE:
<223> OTHER INFORMATION: spacer

<400> SEQUENCE: 113

Pro Gly Pro Gly Pro Gly Pro
1               5

<210> SEQ ID NO 114
<211> LENGTH: 9
<212> TYPE: PRT
<213> ORGANISM: Artificial Sequence
<220> FEATURE:
<223> OTHER INFORMATION: spacer

<400> SEQUENCE: 114

Pro Gly Pro Gly Pro Gly Pro Gly Pro
1               5

<210> SEQ ID NO 115
<211> LENGTH: 11
<212> TYPE: PRT
<213> ORGANISM: Artificial Sequence
<220> FEATURE:
<223> OTHER INFORMATION: spacer

<400> SEQUENCE: 115

Pro Gly Pro Gly Pro Gly Pro Gly Pro Gly Pro
1               5                   10

<210> SEQ ID NO 116
<211> LENGTH: 13
<212> TYPE: PRT
<213> ORGANISM: Artificial Sequence
<220> FEATURE:
<223> OTHER INFORMATION: spacer

<400> SEQUENCE: 116

Pro Gly Pro Gly Pro Gly Pro Gly Pro Gly Pro Gly Pro
1               5                   10

<210> SEQ ID NO 117
<211> LENGTH: 15
<212> TYPE: PRT
<213> ORGANISM: Artificial Sequence
<220> FEATURE:
<223> OTHER INFORMATION: spacer

<400> SEQUENCE: 117

Pro Gly Pro Gly Pro Gly Pro Gly Pro Gly Pro Gly Pro Gly Pro
1               5                   10                  15

<210> SEQ ID NO 118
<211> LENGTH: 17
<212> TYPE: PRT
<213> ORGANISM: Artificial Sequence
```

```
<220> FEATURE:
<223> OTHER INFORMATION: spacer

<400> SEQUENCE: 118

Pro Gly Pro Gly Pro Gly Pro Gly Pro Gly Pro Gly Pro Gly Pro Gly
1               5                   10                  15

Pro

<210> SEQ ID NO 119
<211> LENGTH: 19
<212> TYPE: PRT
<213> ORGANISM: Artificial Sequence
<220> FEATURE:
<223> OTHER INFORMATION: spacer

<400> SEQUENCE: 119

Pro Gly Pro Gly Pro Gly Pro Gly Pro Gly Pro Gly Pro Gly Pro Gly
1               5                   10                  15

Pro Gly Pro

<210> SEQ ID NO 120
<211> LENGTH: 21
<212> TYPE: PRT
<213> ORGANISM: Artificial Sequence
<220> FEATURE:
<223> OTHER INFORMATION: spacer

<400> SEQUENCE: 120

Pro Gly Pro Gly Pro Gly Pro Gly Pro Gly Pro Gly Pro Gly Pro Gly
1               5                   10                  15

Pro Gly Pro Gly Pro
            20
```